United States Patent [19]

Eistetter et al.

[11] 4,279,918

[45] Jul. 21, 1981

[54] 2-(NUCLEARLY-SUBSTITUTED)BENZYL-PYRROLIDINES

[75] Inventors: Klaus Eistetter; Hartmann Schaefer; Heinz G. Menge, all of Constance, Fed. Rep. of Germany

[73] Assignee: Byk Gulden Lomberg Chemische Fabrik G.m.b.H., Constance, Fed. Rep. of Germany

[21] Appl. No.: 819,460

[22] Filed: Jul. 27, 1977

[30] Foreign Application Priority Data

Jul. 28, 1976 [LU] Luxembourg .......................... 75478

[51] Int. Cl.³ ............... C07D 207/108; C07D 207/09; C07D 207/10; A61K 31/40
[52] U.S. Cl. ........................ 424/274; 260/326.5 E; 260/326.5 M; 260/326.47; 260/326.81; 260/326.84; 260/326.85; 260/326.87
[58] Field of Search ................ 260/326.5 M, 326.47, 260/326.5 E, 326.81, 326.84, 326.85, 326.87; 424/274

[56] References Cited

U.S. PATENT DOCUMENTS 3,644,414  2/1972  Helsley ........................... 260/326.85

Primary Examiner—Anton H. Sutto
Assistant Examiner—D. B. Springer
Attorney, Agent, or Firm—Berman, Aisenberg & Platt

[57] ABSTRACT

2-Benzylpyrrolidines bearing from 1 to 4 nuclear substituents on the benzyl ring are pharmacologically active, particularly on the CNS, on blood pressure and on pain sensation for warm-blooded animals. They are synthesized, e.g., by reducing appropriate 2-benzylpyrrolidines and are formulated into medicament compositions according to established conventional techniques.

36 Claims, No Drawings

2-(NUCLEARLY-SUBSTITUTED)BENZYLPYRROLIDINES

RELATED APPLICATION

The subject matter of the hereindisclosed invention bears a relationship to that of concurrently-filed application Ser. No. 819,453 having a common inventor.

BACKGROUND

German Patent Specification 1,049,380 [*Chem. Abstr.* 55 (1961)P4532c] refers to a process for preparing α-substituted pyrrolidines of formula A

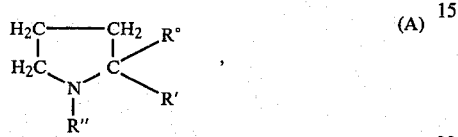

in which
R° denotes a hydrogen atom, alkyl, aryl, aralkyl or a heterocyclic radical;
R' denotes alkyl, aryl, aralkyl, a heterocyclic radical or cyano; and
R'' denotes a hydrogen atom or a monovalent organic radical.

The compounds obtained according to this process are intended to be used as medicaments; no specific action is assigned to them and α-phenylpyrrolidine is the sole cited example.

In the course of synthesizing nicotine analogues, J. H. Burckhalter and J. H. Short [*J. Org. Chem.* 23 (1958) 1281–86] refer to 2-benzylpyrrolidine and to 2-benzyl-1-methylpyrrolidine and draw attention to publications of D. F. Starr et al. [*J. Amer. Chem. Soc.* 54 (1932) 3971] and cf. R. Lukeš [*Chem. Listy* 27 (1933) 392, 409; *Chem. Abstr.* 29 (1935) 1720]. 2-Benzyl-1-methylpyrrolidine was obtained in a low yield by Fery and van Hove [*Bull. Soc. chim. Belg.* 69 (1960) 63–78; *Chem. Abstr.* 55 (1961) 4475d] through rearrangement of 1-methyl-1-benzylpyrrolidinium iodide. Within the scope of their work on rearranging α-aminoketones during a Clemmensen reduction, N. J. Leonard et al. [*J. Amer. Chem. Soc.* 75 (1953) 3727–30] describe preparing 1-ethyl-2-benzylpyrrolidine without stating any pharmacological activity for the latter substance. 2-benzylpyrrolidine showed no activity with regard to hypertension caused by adrenalin; 2-benzyl-1-methylpyrrolidine caused only a partial reduction of hypertension induced by adrenalin. Any anti-hypertensive utility of either of the last two noted compounds is highly doubtful and such utility, if it does exist, is expected to be severely limited in extent. German Offenlegungsschrift (Published Specification) 25 48 053 [Derwent, Pharmdoc Basic Number 36351X/20] refers to saturated α-substituted benzyl-1-benzhydrylazaheterocyclic compounds, in particular α-substituted benzyl-1-benzhydrylazetidines for treating obesity.

SUMMARY OF THE INVENTION

Substituted 2-benzylpyrrolidines, their quaternary alkylpyrrolidinium compounds and their acid-addition salts are pharmacologically-active compounds which act on the central nervous system (CNS), on blood pressure and on pain sensation of warm-blooded animals. They are prepared according to various processes, e.g. through reduction of appropriate 2-benzylpyrrolidines, functionalization of corresponding 2-benzylpyrrolidines or reduction of N-acyl-2-benzylpyrrolidines. They are conventionally compounded into medicament compositions and administered, e.g., orally to warm-blooded animals, such as humans.

The compounds of the invention have a 5-membered nitrogen-containing ring and a substituted-phenyl ring; they comprise compounds of formula I:

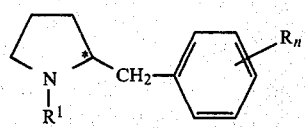

wherein
$R^1$ is $[-H]_{(2-a)}[(\text{aliphatic hydrocarbyl})_{(2-b)}\{(\text{alicyclic hydrocarbyl})_{(2-c)}[(\text{cycloalkylalkyl})_{(2-d)}\{(\text{aralkyl})_{(2-e)}(\text{substituted aralkyl})_{(e-1)}\}_{(d-1)}]_{(c-1)}\}_{(b-1)}]_{(a-1)}$;
each R is, independently, $[\text{halo}]_{(2-f)}[(\text{alkyl})_{(2-g)}\{(-\text{OH})_{(2-h)}[(\text{alkoxy})_{(2-i)}\{(\text{acyloxy})_{(2-j)}[(-\text{NH}_2)_{(2-k)}\{(\text{monosubstituted amino})_{(2-m)}[(\text{disubstituted amino})_{(2-p)}\{(-\text{NO}_2)_{(2-r)}[(\text{phenyl})_{(2-s)}(\text{substituted phenyl})_{(s-1)}]_{(r-1)}\}_{(p-1)}]_{(m-1)}\}_{(k-1)}]_{(j-1)}\}_{(i-1)}]_{(h-1)}\}_{(g-1)}]_{(f-1)}$;
each of a, b, c, d, e, f, g, h, i, j, k, m, p, r and s is, independently, a positive whole number of at most 2; and
n is a positive whole number of at most 4;
their enantiomers, racemic mixtures, quaternary alkylpyrrolidinium counterparts and acid-addition salts.

DEFINITIONS

Throughout the disclosure and claims a number of terms appear and reappear. For convenience, a glossary of some of these terms and of their meanings, as used throughout this text, is provided.

acid-addition salt—a salt formed by a salt-forming group, such as a tertiary amine, and an acid, wherein the acid is, for example, an organic acid, e.g. tartaric acid; an inorganic acid, e.g. hydrochloric acid, hydrobromic acid and sulfuric acid; a monobasic acid, such as an alkanesulfonic acid, e.g. methanesulfonic acid (H$_3$C—SO$_3$H); a dibasic acid, e.g. succinic acid; a tribasic acid, e.g. phosphoric acid and citric acid; a saturated acid, e.g. acetic acid, an ethylenically unsaturated acid, e.g. maleic acid and fumaric acid; and an aromatic acid, e.g. salicylic acid and arylsulfonic acids, such as benzenesulfonic acid; all references to organic or inorganic acids include the entire scope thereof unless otherwise limited. Pharmacologically-compatible salts of inorganic and of organic acids usually employed in Galenic practice are of primary interest. Pharmacologically-incompatible salts are readily converted into pharmacologically-compatible salts by conventional well-established processes. Illustrative pharmacologically-acceptable water-soluble and water-insoluble acid-addition salts include the hydrochloride, hydrobromide, hydriodide, phosphate, nitrate, sulfate, acetate, citrate, gluconate, benzoate, hibenzate [2-(4-hydroxybenzoyl)benzoate], fendizoate [o-{(2'-hydroxy-4-biphenylyl)carbonyl}-benzoate], propionate, butyrate, sulfosalicylate, maleate, malate, fumarate, succinate, oxalate, tartrate, amsonate [4,4'-diaminostilbene-2,2'-disulphonate], embonate [1,1'-methylene-bis-2-hydroxy-3-naphthoate], metembonate, stearate, tosilate [p-toluenesulfonate], 2-hydroxy-3-naphthoate, 3-hydroxy-2-naphthoate, mesilate [methanesulfonate]; further, salts with bumetanide [3-(butylamino)-4-phenoxy-5-sulfamoylbenzoic acid], furosemide [4-chloro-N-furfuryl-5-sulfamoylanthranilic acid], besunide [4-benzyl-3-(butylamino)-5-sulfamoylbenzoic acid], piretanide [4-phenoxy-3-(1-pyrrolidinyl)-5-sulfamoylbenzoic acid], etacrynic acid [{2,3-dichloro4-(2-methylenebutyryl)phenoxy}acetic acid] and tienilinic acid [{2,3-dichloro-4-(2-thenoyl)phenoxy}acetic acid].

acyl—a radical based on any organic acid, e.g. CS—R* and —CO—R*, wherein each R* is alicyclic hydrocarbyl (cycloalkyl, e.g. cyclohexyl), cycloalkylalkyl (e.g. cyclopropylmethyl), hydrocarbyl, aralkyl (e.g. benzyl) or hydrocarbyl aryl (e.g. phenyl), preferably aliphatic hydrocarbyl (alkyl, e.g. methyl or ethyl).

acyloxy—an acyl radical (as previously defined) bound to another group through an oxygen bridge, especially —O—CO—R$^1$ and most suitably alkanoyloxy with from 1 to 7, more particularly with from 2 to 5, carbon atoms; acetoxy is the preferred acyloxy radical.

alicyclic—saturated, e.g. cycloalkyl, or aliphatically-unsaturated, e.g. cycloalkenyl, radicals having from 3 to 7 ring carbon atoms, such as cyclopropyl, cyclobutyl, cyclopentyl, cyclohexyl, cyclohexenyl and cycloheptyl, of which cycloalkyl, particularly those with 5 or 6 ring carbon atoms, are preferred.

aliphatic—an open-chain, linear or branched, substituted or unsubstituted, saturated or unsaturated (ethylenically, e.g. alkenyl, such as allyl, and/or acetylenically, e.g. alkynyl, such as propargyl) carbon-based radical (optionally having one or more hetero atoms and up to 7 carbon atoms unless otherwise specified), e.g. alkyl, alkoxy and alkanoyl.

alkalize—render basic; adjust the pH to one which is in excess of 7.0, preferably 10 to 12.

alkenyl—both straight-chain and branch-chain mono- or poly-olefinically-unsaturated, preferably not more than di-olefinically-unsaturated, hydrocarbyl having a single available bond, having no triple bonds and containing from 3 to 7 carbon atoms unless otherwise limited, e.g. allyl, 2-methylallyl, buten-2-yl, penten-2-,3- or 4-yl, hexen-2-,3-,4- or 5-yl, hepten-2-,3-,4-,5- or 6-yl and pentadien-2,4-yl.

alkinyl—alkynyl; both straight-chain and branch-chain unsaturated hydrocarbyl having at least one triple bond and from 3 to 7 carbon atoms, e.g. propin-2-yl.

alkoxy—alkyloxy and alkylenedioxy; alkyl bound to another group through an oxygen bridge, e.g. methoxy, ethoxy, propoxy, isopropoxy, butoxy, isobutoxy, secondary butoxy and tertiary butoxy. Those with from 1 to 4, and particularly with from 1 to 3, carbon atoms, especially methoxy, are preferred; also, saturated (preferably straight-chain) aliphatic hydrocarbyl directly bound, by the same or different carbon atoms, to two oxygen atoms, each of which has an available bond, e.g. methylenedioxy, 1,2-ethylenedioxy, and 1,1-, 1,2- or 1,3-propylenedioxy or 2,2-dimethyl-1,3-propylenedioxy.

alkyl—straight-chain or branch-chain saturated aliphatic hydrocarbon radical having a single available bond and suitably containing from 1 to 7 carbon atoms, e.g. methyl, ethyl, propyl, isopropyl, butyl, secondary butyl, tertiary butyl, pentyl, hexyl and heptyl, unless otherwise limited; those with from 1 to 5, particularly with from 1 to 3, and above all with 1 or 2, carbon atoms are preferred. Branched alkyl radicals with from 3 to 7 carbon atoms are, e.g., isopropyl, sec.-butyl, tert.-butyl, 3-methylbutyl, 2,2-dimethylpropyl, 2-methylpentyl, 3,3-dimethylbutyl or 2-ethyl-3-methylbutyl, of which those with from 3 to 5, above all with 3 or 4, carbon atoms are preferred.

alkylenedioxy—a substituent which is a form of alkoxy wherein two oxygen atoms, each having an available bond, are directly bound to the same or different carbon atoms of saturated (preferably linear) hydrocarbyl; when the saturated hydrocarbyl is straight chain and has more than one carbon atom, the two oxygen atoms are preferably α,ω-bound thereto, as in 1,2-ethylenedioxy; when the two oxygen atoms are bound to the same carbon atom, as in 1,1-ethylenedioxy (ethylidenedioxy), the substituent is alternatively referred to as alkylidenedioxy; when this substituent is bound to a carbocyclic aromatic ring, it is necessarily bound to two different and preferably (but not necessarily) adjacent ring carbon atoms; when it is a substituent of the substituted benzyl ring of formula I, it takes the place of two R's, as in 3,4-methylenedioxybenzyl.

amino—the H$_2$N-radical, which may be substituted by replacing one or both of the hydrogen atoms.

aralkyl—aryl-substituted alkyl wherein the aryl is hydrocarbyl (optionally-substituted) aryl having up to 12 ring carbon atoms, e.g. phenyl, α-naphthyl, β-naphthyl and biphenyl, and the alkyl (preferably methyl) advantageously has from 1 to 4 carbon atoms. Substituted or unsubstituted radicals wherein the aryl is phenyl, e.g. phenethyl, phenylpropyl and, especially, benzyl (or their nuclearly-substituted counterparts), are preferred.

aryl—a substituted or unsubstituted monovalent unsaturated aromatic carbocyclic radical having a single ring, e.g. phenyl, or 2 or 3 condensed rings, e.g. β-naphthyl and 3-acenaphthylenyl, having a total of at most 12 ring members; each aromatic ring having from 5 to 7 ring members; phenyl is preferred.

asymmetric carbon—a carbon atom, conventionally designated by an asterisk (*), which has four different radicals or atoms attached to it.

cycloalkyl—a saturated carbocyclic hydrocarbyl ring having from 3 to 7 ring carbon atoms, one of which has a single available valence, e.g. cyclopentyl and cyclohexyl.

cycloalkylalkyl—alkyl having from 1 to 4, preferably 1 or 2, carbon atoms and substituted by cycloalkyl having from 3 to 7, preferably 3 to 5, ring carbon atoms. Illustrative examples are cyclopropylmethyl and cyclobutylmethyl.

free-base form—a compound or radical having at least one amino-nitrogen atom, and wherein each such nitrogen atom is a primary, secondary or tertiary amino nitrogen atom.

functional group—a group responsible for common properties.

functionalization—introduction or removal of a functional group, e.g. —OH, halo, (substituted or unsubstituted) amino, nitro, ether, ester, acyl, oxo or amide, into or from the molecular structure; introduction is illustrated by nitration, removal is illustrated by ether cleavage.

halo—fluoro, chloro, bromo or iodo; preferably fluoro, chloro or bromo, especially chloro.

hydrocarbyl—an organic (hydrocarbon) radical ordinarily (but not necessarily) having a single available bond and composed entirely of hydrogen and carbon atoms; such radicals are either substituted or unsubstituted, as specified; they are (saturated, ethylenically unsaturated and/or acetylenically unsaturated) aliphatic, (saturated or unsaturated) cycloaliphatic (i.e. alicyclic), cycloaliphaticaliphatic, homocyclic (single- or multiple-condensed-ring) aromatic or aromaticaliphatic.

lower—restricts a radical to which it is applied to one having at most seven carbon atoms. Throughout the subject disclosure and claims all aliphatic, alkyl, alkoxy (including alkylenedioxy), acyl and acyloxy radicals are "lower" radicals (having at most 7 carbon atoms) unless otherwise specified.

quaternary alkylpyrrolidinium—a quaternary ammonium compound (including ammonium salts and ammonium bases, but not acid-addition salts) or radical wherein the quaternary nitrogen is that of a saturated ring having four carbon atoms and one nitrogen atom as the sole ring members. Suitable quaternary alkylpyrrolidinium groups are alkylpyrrolidinium hydroxides; halides, for example iodides, bromides and chlorides; sulfonates, for example p-toluenesulfonates; and sulfates, for example methyl-sulfates. The alkyl of the alkylpyrrolidinium ordinarily has from 1 to 7 carbon atoms. Alkylpyrrolidinium iodides in which the alkyl has up to 4 carbon atoms, and particularly those in which the alkyl has only 1 carbon atom, are preferred.

radical—A group of atoms that behaves as a single atom in a chemical reaction or that remains unchanged during one or a series of reactions; throughout the instant disclosure a radical has only one binding valence bond unless otherwise defined.

substituted—bearing one or more substituents; the benzyl of 2-benzylpyrrolidines of formula I or Ia is nuclearly substituted by from 1 to 4 substituents, e.g. those designated R, $R^2$, $R^3$, $R^4$ and $R^5$; any aralkyl is optionally substituted [preferably nuclearly mono-substituted by, e.g., halo (p-chlorobenzyl), m-chlorobenzyl, p-bromobenzyl, o-fluorobenzyl or p-fluorobenzyl), alkyl having from 1 to 4 carbon atoms (p-methylbenzyl) or alkoxy having from 1 to 4 carbon atoms (p-methoxybenzyl) or substituted in the alkyl by, e.g., hydroxyl (4-hydroxy-4-phenylbutyl) or oxo {benzoylmethyl, 2-benzoylethyl, 3-benzoylpropyl, preferably 3-(p-chlorobenzoyl)propyl and particularly 3-(p-fluorobenzoyl)propyl}]; optionally-substituted phenyl is substituted, e.g., independently (at one or more positions) preferably by halo (p-chlorophenyl and p-fluorophenyl), hydroxyl (p-hydroxyphenyl), alkyl having from 1 to 4 carbon atoms (p-tolyl) or alkoxy having from 1 to 4 carbon atoms (p-methoxyphenyl); any contemplated substitution is either mono- or poly-substitution, the only limitation of which is steric hindrance, the conditions for which are well known and readily understood by every artisan.

substituted amino—substituents of mono (wherein one hydrogen atom of —$NH_2$ is replaced) or of di (wherein both hydrogen atoms of —$NH_2$ are replaced) -substituted amino independently include alkyl and acyl (particularly alkylamino having from 1 to 4, preferably 1 or 2, carbon atoms, dialkylamino having from 1 to 4, preferably 1 or 2, carbon atoms in each alkyl and acylamino, such as alkanoyl amino having from 2 to 5 carbon atoms), as well as the usual groups (tosyl, mesyl, anisyl, brosyl, nisyl, trityl, benzyl and benzyloxycarbonyl) employed for protecting amino groups.

substituted aralkyl—optionally poly-, but preferably nuclearly mono-substituted by, e.g., halo (particularly fluoro, chloro or bromo), alkyl having from 1 to 4 carbon atoms and/or alkoxy having from 1 to 4 carbon atoms, e.g. p-chlorobenzyl, m-chlorobenzyl, p-bromobenzyl, o-fluorobenzyl, p-fluorobenzyl, p-methylbenzyl and p-methoxybenzyl. Substitution is additionally or alternatively in the alkyl of aralkyl as in arylhydroxyalkyl and aryloxoalkyl, such as benzoylmethyl, 2-benzoylethyl, 3-benzoylpropyl, but preferably 3-(p-chlorobenzoyl)propyl and, in particular, 3-(p-fluorobenzoyl)propyl.

substituted phenyl—phenyl independently substituted in one or more available positions by halo, hydroxyl, alkyl having from 1 to 4 carbon atoms and/or alkoxy having from 1 to 4 carbon atoms; monosubstituted and p-substituted phenyl, such as p-chlorophenyl, p-fluorophenyl, p-hydroxyphenyl and p-methoxyphenyl, being preferred.

DETAILS

The compounds, in free-base form, are alternatively depicted as those of formula Ia:

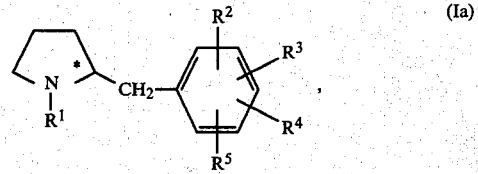

wherein
$R^1$ denotes a hydrogen atom, straight-chain or branched aliphatic or alicyclic hydrocarbyl, cycloalkylalkyl or optionally-substituted aralkyl;
$R^2$ denotes halo, alkyl, hydroxyl, alkoxy, acyloxy, optionally-substituted amino, nitro, or optionally-substituted phenyl; and
each of $R^3$, $R^4$ and $R^5$ is, independently, a hydrogen atom, halo, alkyl, hydroxyl, alkoxy, acyloxy, optionally-substituted amino, nitro or optionally-substituted phenyl;

their enantiomers and racemic mixtures. As all compounds of formula Ia have an asymmetric carbon atom (designated by an asterisk), such compounds have optically-active isomers. The respective antipodes and mixtures thereof are within the scope of the present invention.

A special group of substituted 2-benzylpyrrolidines of formula Ia comprises those compounds:
wherein
$R^1$ denotes a hydrogen atom (-H), a straight-chain or branched aliphatic hydrocarbon radical (hydrocarbyl) with from 1 to 5 carbon atoms, cycloalkylalkyl with 1 or 2 carbon atoms in the alkyl radical and from 3 to 5 carbon atoms in the cycloalkyl radical, or optionally mono-substituted phenylalkyl with from 1 to 4 carbon atoms in the alkyl radical;
$R^2$ denotes halo, hydroxyl (—OH), alkyl with from 1 to 4 carbon atoms, alkoxy with from 1 to 4 carbon atoms, alkanoyloxy with from 2 to 5 carbon atoms, amino (—$NH_2$), dialkylamino with 1 to 2 carbon atoms per alkyl radical, nitro (—$NO_2$) or phenyl which is optionally substituted in the p-position; and each of $R^3$, $R^4$ and $R^5$ is, independently, a hydrogen atom, halo, hydroxyl, alkyl with from 1 to 4 carbon atoms, alkoxy with from 1 to 4 carbon atoms, alkanoyloxy with from 2 to 5 carbon atoms, amino, dialkylamino with 1 or 2 carbon atoms per alkyl radical or nitro, the benzyl nucleus being unsubstituted in at least one of the ortho (2- and 6-) positions;

their quaternary ($C_1$–$C_4$) alkylpyrrolidinium compounds and their acid-addition salts.

Of this group attention is especially directed to those substituted 2-benzylpyrrolidines in which at least one and preferably two of the $R^3$, $R^4$ and $R^5$ denote a hydrogen atom.

Particular substituted 2-benzylpyrrolidines of even this more-limited group are those
wherein $R^1$ denotes a hydrogen atom, straight-chain alkyl with from 1 to 3 carbon atoms, branched alkyl with from 3 to 5 carbon atoms, cycloalkylmethyl with from 3 to 5 carbon atoms in the cycloalkyl group or benzyl which is optionally substituted in the p-position by halo, methyl or methoxy;

$R^2$ denotes halo, hydroxyl, methoxy, amino or nitro; and $R^3$ denotes a hydrogen atom, halo, hydroxyl, methoxy, amino or nitro, $R^2$ and $R^3$ preferably being in the 2-, 3- and/or 4-position; and each of $R^4$ and $R^5$ is a hydrogen atom;
and their methylpyrrolidinium compounds and their pharmacologically-compatible acid-addition salts.

Of the particular substituted 2-benzylpyrrolidines those in which $R^1$ denotes a hydrogen atom, methyl, isopropyl, tert.-butyl, cyclopropylmethyl or benzyl and their pharmacologically-compatible acid-addition salts are regarded as select.

The preferred of the select substituted 2-benzylpyrrolidines are those
wherein
$R^1$ denotes a hydrogen atom, methyl, isopropyl or cyclopropylmethyl;

$R^2$ denotes a 2-, 3- or 4-positioned fluoro, chloro, hydroxy, methoxy or amino substituent; and $R^3$ is a hydrogen atom;
and their pharmacologically-acceptable acid-addition salts.

Illustrative compounds according to the invention are
2-(2-chlorobenzyl)-1-methylpyrrolidine,
2-(4-chlorobenzyl)-1-methylpyrrolidine,
2-(3-methoxybenzyl)-1-methylpyrrolidine,
2-(3-hydroxybenzyl)-1-methylpyrrolidine,
2-(3-chlorobenzyl)-1-methylpyrrolidine,
2-(2-methoxybenzyl)-1-methylpyrrolidine,
in particular, 2-(4-aminobenzyl)-1-methylpyrrolidine and 2-(4-chlorobenzyl)pyrrolidine,
and their pharmacologically-compatible acid-addition salts. The following additional exemplary compounds of this invention, like the previously-noted ones, are prepared according to procedures described herein from known starting materials or from materials which are readily synthesized according to analogy procedures from available starting materials:
2-[3,5-dichloro-4-(p-methoxyphenyl)benzyl]-1-propargyl-pyrrolidine,
1-butyl-2-[3-(p-chlorophenyl)-5-methoxybenzyl]pyrrolidine,
2-[2-amino-5-methoxybenzyl]-1-cyclohexylpyrrolidine,
1-benzyl-2-(3-isopropyl-4-methylbenzyl)pyrrolidine,
2-(2,4,5-trichlorobenzyl)-1-methylpyrrolidine,
2-(3,4-dichlorobenzyl)-1-allylpyrrolidine,
2-(4-amino-3-chloro-2-methylbenzyl)pyrrolidine,
2-(5-isopropyl-3-methoxybenzyl)-1,1-diethylpyrrolidinium iodide.

OPTICAL ACTIVITY

The substituted 2-benzylpyrrolidines of formula Ia possess a chirality center at the carbon atom characterized by (*). The invention therefore includes both the racemates and the enantiomers and their mixtures.

UTILITY

The substituted 2-benzylpyrrolidines of formulae I and Ia, the corresponding alkylpyrrolidinium compounds and the pharmacologically-compatible acid-addition salts possess valuable properties which render them commercially exploitable. In the first place, the compounds, 2-benzylpyrrolidine, the 2-benzyl-1-alkylpyrrolidines, the corresponding alkylpyrrolidinium compounds and the pharmacologically, i.e. biologically, compatible salts have distinct pharmacological properties; in particular, effects on the central nervous system (CNS), on blood pressure and on sensation of pain and, secondly, they are readily converted into other substituted 2-benzylpyrrolidines of formulae I and Ia and therefore represent valuable intermediates for the preparation of pharmacologically-active compounds of formulae I and Ia and of their alkylpyrrolidinium compounds and their pharmacologically-compatible salts.

The CNS effectiveness of the 2-benzylpyrrolidines, the alkylpyrrolidinium compounds and the pharmacologically-compatible salts is useful for CNS stimulation, increased vigilance and promotion of normal and of pathologically-inhibited drive. In addition, some of the subject compounds exhibit a strong analgesic effect or an action which influences blood pressure.

The excellent and broad pharmacological effectiveness of the 2-benzylpyrrolidines makes them useful in both human and veterinary medicine; they are useful for prophylaxis before symptoms occur or for the treatment of symptoms which have already appeared.

In the sphere of medicine for humans (for both men and women) compounds of this invention are useful for counteracting such indications as lack of drive, reduced vigilance, depression, organic psychosyndromes in the case of cerebral retrogression processes, lack of vitality, blood-pressure troubles and exhaustion states, as well as difficulties in learning.

In the field of veterinary medicine, the indications are reduced vitality and pain states; with regard to these the compounds are useful for treating higher animals, such as economically-useful animals and domestic animals.

The compounds of formulae I and Ia exhibit an activity spectrum wherein the activity on CNS is emphasized. The particular spectrum, however, for any specific compound has focal points dependent upon the nature of the actual substitution. Central stimulating activity is clearly emphasized, for example, in the spectrum for 2-(3-methoxybenzyl)-1-methylpyrrolidine, whereas the analgesic effect is emphasized, for example, in the spectrum for 2-(2-methoxybenzyl)-1-methylpyrrolidine, and the effect which influences blood pressure, for example, in the spectra for 2-(2-chlorobenzyl)-1-methylpyrrolidine and for 2-(3,4-dihydroxybenzyl)-1-methylpyrrolidine. A combination of these effects is emphasized in different embodiments. Analgesic and central-stimulating activities are emphasized, for example, in the spectra for 2-(4-chlorobenzyl)pyrrolidine, 2-(4-chlorobenzyl)-1-methylpyrrolidine, 2-(4-chlorobenzyl)-1-isopropylpyrrolidine and 2-(4-aminobenzyl)-1-methylpyrrolidine, whereas the effect which stimulates centrally and that which influences blood pressure are emphasized, for example, in the spectrum for 2-(3-hydroxybenzyl)-1-methylpyrrolidine.

Depending on the desired therapeutic objective, one or any combination of the 2-benzylpyrrolidines are used.

According to the invention, the active substances are useful in human and veterinary medicine in any desired form and virtually through any recognized route or mode of administration, e.g. systemically or topically, suitable for forming and/or maintaining a sufficient blood or tissue level or local concentration of the 2-benzylpyrrolidine. Such is achieved, e.g., by oral, rectal or parenteral administration in suitable doses. The new medicaments are also locally administrable. Advantageously, a pharmaceutical preparation of active substance (according to this invention) is in the form of a unitary dose which is matched to the desired or contemplated mode of administration. A unitary dose is, for example, in the form of a tablet, a dragee, a capsule, a suppository or a measured volume of a powder, a granulate, a solution, an emulsion, a suspension, a sol or a gel.

By "unitary dose" in the sense of the present invention is understood a physically specified unit which contains an individual amount of the active constituent in combination with a pharmaceutical excipient, the active-substance content of which specified unit corresponds to a fraction of, or to a multiple of, a therapeutic individual dose. An individual dose preferably contains the amount of active substance which is administered at one application and which normally corresponds to a whole, a half, a third or a quarter of the daily dose. When only a fraction, such as one half or a quarter, of the unitary dose is needed for an individual therapeutic administration, the unitary dose is advantageously divisible, e.g., in the form of a tablet with break score.

In general, both in human and in veterinary medicine, it is advantageous to administer the active substance or substances, in the case of oral administration, in a daily dose of from about 0.06 to about 12, preferably from 0.14 to 5.7, and in particular from 0.3 to 3, mg/kilogram (kg) of body weight in the form of several, preferably 1 to 3, individual administrations (where appropriate) to achieve the desired results. Each individual administration contains the active substance or substances in an amount of from about 0.01 to about 3.0, preferably from 0.04 to 1.5, in particular from 0.07 to 0.7, mg/kg of body weight.

For parenteral treatment, e.g., in the case of acute depression or a severe pain state, similar dosages apply; from about 1 to about 50 mg of active substance are administered.

Therapeutic administration of a pharmaceutical preparation according to this invention, in the case of long-term medication, is generally effected at fixed points in time, such as 1 to 4 times daily, e.g. after each meal and/or in the evening. In acute cases, medication occurs at a varying point in time, as required. Particular circumstances may necessitate deviation from the noted dosages, depending on the nature, body weight and age of the subject being treated, the nature and gravity of the illness, the nature of the particular preparation, the mode of administration of the medicament and the space of time or interval (frequency) within which administration occurs. Thus, less than the previously-mentioned amount of active substance is adequate for some cases, whereas other cases require more than the mentioned amount of active substance. Establishing the optimum dosage and type of application of active substances required in each case is readily effected by the skilled man on the basis of his specialized knowledge.

A further subject matter of the invention is a process for the treatment of mammals which are suffering from primary or secondary disturbances of the central nervous system or from pathological changes of blood pressure or from pain states which is characterized by administering to an affected mammal a CNS-effective or blood-pressure-influencing or analgesic and pharmacologically-compatible amount of one or more 2-benzylpyrrolidines and/or their pharmacologically-compatible salts.

MEDICAMENT COMPOSITIONS

The subject invention also involves medicament which contains 2-benzylpyrrolidines of formula Ia wherein
$R^1$ denotes a hydrogen atom (—H), straight-chain or branched aliphatic or alicyclic hydrocarbyl, cycloalkylalkyl or aralkyl; and
each of $R^2$, $R^3$, $R^4$ and $R^5$ is, independently, a hydrogen atom, halo, alkyl, hydroxyl, alkoxy, acyloxy, optionally-(mono- or di-)substituted amino, nitro or optionally-substituted phenyl;
their quaternary alkylpyrrolidinium compounds and/or their pharmacologically-compatible acid-addition salts.

Preferred medicaments are those which contain (nuclearly-substituted)benzylpyrrolidines, particularly those of the previously-noted special group and of the selected subgroups therein, and/or the pharmacologically-compatible acid-addition salts.

The medicaments are prepared according to methods which are known per se. As medicaments, the new compounds are useful as such or in combination with suitable pharmaceutical excipients. When the new pharmaceutical preparations contain pharmaceutical excipient in addition to active ingredient, the active-ingredient content is from 5 to 95, preferably from 25 to 75, percent by weight of the total mixture which constitutes such preparations.

Pharmaceutical preparations according to the invention contain, when they are present in unitary doses and are intended for application, e.g., to humans, from about 1 to 200, advantageously from 2.5 to 100 and, in particular, from 5 to 50, milligrams (mg) of active [2-benzylpyrrolidine and/or 2-(nuclearly-substituted)benzylpyrrolidine] substance.

Preparations in a pharmacologically-compatible, e.g. aqueous, solution and which contain from about 0.1 to about 5, preferably from 0.2 to 3, in particular from 0.5 to 2, percent by weight of active substance are suitable for local application.

Pharmaceutical preparations generally comprise the active substance according to the invention and non-toxic, pharmaceutically-compatible medicament excipients which are useful as additive or diluent in solid, semi-solid or liquid form or as surrounding agent, for example in the form of a capsule, a tablet coating, a bag or other container for the therapeutically-active constituent. An excipient serves, e.g., as medium to assist absorption of the medicament by the body, as a formulation auxiliary, as a sweetener, as a taste corrector, as coloring matter or as a preservative.

For oral application, e.g., tablets, dragees, hard and soft capsules, e.g. of gelatin, dispersible powders, granulates, aqueous and oily suspensions, emulsions, solutions or syrups are useful. Each is made according to established procedures and known formulations from the active ingredient(s) and available starting materials.

Tablets contain, e.g., inert diluent, such as calcium carbonate, calcium phosphate, sodium phosphate or lactose; granulation and/or distribution agent, such as maize starch or alginates; binder, such as starch, gelatin or acacia gum; and glidant or lubricant, such as aluminum stearate or magnesium stearate, talc or silicone oil. They are optionally coated, e.g., with a coating which may be of such a nature as to produce a delayed decomposition and resorption of the medicament in the gastrointestinal tract; better compatibility, protraction or a retardation is thus achievable. Gelatin capsules optionally contain the medicament mixed with a solid diluent, e.g. calcium carbonate or kaolin, or with an oily diluent, e.g. olive oil, arachis oil or paraffin oil.

Aqueous suspensions optionally contain suspending agents, e.g. sodium carboxymethylcellulose, methylcellulose, hydroxypropylcellulose, sodium alginate, polyvinylpyrrolidone, gum tragacanth or acacia gum; dispersing and wetting agents, e.g. polyoxyethylene stearate, heptadecaethyleneoxycetanol, polyoxyethylene sorbitol monooleate, polyoxyethylenesorbitan monooleate or lecithin; preservatives, e.g. methyl or propyl hydroxybenzoates; flavorings; sweeteners, e.g. sucrose, lactose, sodium cyclamate, dextrose or invert sugar syrup. Oily suspensions optionally contain, e.g., arachis, olive, sesame, coconut or paraffin oil; thickeners, such as beeswax, hard paraffin or cetyl alcohol; as well as sweeteners, flavoring and anti-oxidants.

Powders and granulates dispersible in water optionally contain the active ingredient mixed with dispersing, wetting and suspending agents, e.g. those previously mentioned, and sweetener, flavoring and coloring.

Emulsions optionally contain, e.g., olive, arachis or paraffin oil as well as emulsifiers, such as acacia gum, gum tragacanth, phosphatides, sorbitan mon-oleate or polyoxyethylenesorbitan mono-oleate, in addition to sweetener and flavoring.

Binder, such as cocoa butter or polyethyleneglycol, which melts at rectal temperature, is used to produce suppositories.

Sterile injectable aqueous suspensions and isotonic salt or other solutions which optionally contain dispersing or wetting agents and/or pharmacologically-compatible diluents, e.g. propyleneglycol or butyleneglycol, are suitable for parenteral administration of active ingredients referred to herein.

Gels, sols or tablets suitable for local treatment (with subject active ingredients) optionally contain, in addition to the active substance or substances, the usual excipients, e.g. animal and vegetable fats, waxes, paraffins, starch, tragacanth, cellulose derivatives, polyethyleneglycols, silicones, bentonites, silicic acid, talc and zinc oxide or mixtures of these substances.

Powders and sprays for administering subject active ingredients optionally contain the usual excipients, e.g. lactose, talc, silicic acid, aluminum hydroxide, calcium silicate and polyamide powder or mixtures of these substances, in addition to active substance or substances. Sprays also optionally contain the usual propellants, e.g. chlorofluorohydrocarbons.

The active substance or substances, where appropriate with one or more of the above-mentioned excipients, are provided in microencapsulated form.

Besides the 2-benzylpyrrolidines, pharmaceutical preparations within the scope of this invention optionally contain, for example, one or more pharmacologically-active (chemically- and pharmacologically-compatible) constituents from other groups of medicaments, for example mild stimulants, such as caffeine; analgesics, such as aminophenazone, acetylsalicylic acid or d-propoxyphen; antidepressants, dibenzepin, doxepin, maprotilin, amitriptylin, notriptylin or melitracen; tranquilizers, such as meprobamate, benzodiazepines, e.g. diazepam, chlordiazepoxide; agents which promote cerebral blood circulation and/or tonics, such as glutamic acid, vitamins or combinations thereof.

INTERMEDIATES AND SYNTHESIS

Intermediates of formula I are converted according to well-established methods into pharmacologically-active compounds of formula I, as, e.g., described by the following Examples. Thus, for example, acid-addition salts are obtained from corresponding free bases by reaction with an appropriate acid, and alkylpyrrolidinium compounds are obtained by reaction with, e.g., an appropriate alkyl halide or alkylsulfonate. Ethers, i.e. compounds in which one or more of the substituents $R^2$, $R^3$, $R^4$, $R^5$ represent an alkoxy group (or two, together, represent an alkylenedioxy group) are converted into the corresponding free hydroxy compounds through acid hydrolysis, e.g., with halogen hydride. Esters, i.e. compounds in which each of one or more of substituents $R^2$, $R^3$, $R^4$, $R^5$ represents an acyloxy group, are converted into corresponding free hydroxy compounds by alkaline hydrolysis, e.g., with sodium hydroxide. The free hydroxy compounds, i.e. those in which each of one or more of substituents $R^2$, $R^3$, $R^4$, $R^5$ represents an HO— group, are optionally etherified or esterified according to established and well-known procedures.

Some intermediates are pharmacologically active; e.g. the nitriles of formula IX and their N-alkyl, N-cycloalkyl, N-cycloalkylalkyl and N-aralkyl derivatives are distinguished by analgesic activity with low toxicity. They are useful as analgesics; the dosage forms, the dose to be administered, the mode, route, frequency and duration of administration and application correspond to those previously noted for physiologically-active and pharmacologically-acceptable compounds of formula Ia.

The invention includes a process for preparing the substituted 2-benzylpyrrolidines of formulae I and Ia, which process is characterized by:
(a) a 2-(nuclearly-substituted)benzylpyrrolidine of formula II:

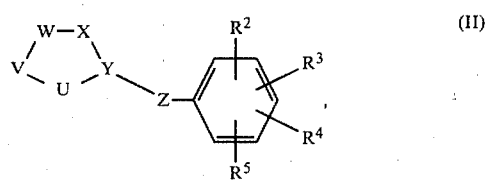

wherein
each of $R^2$, $R^3$, $R^4$ and $R^5$ has its previously-ascribed meaning;

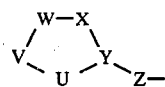

denotes one of the groupings

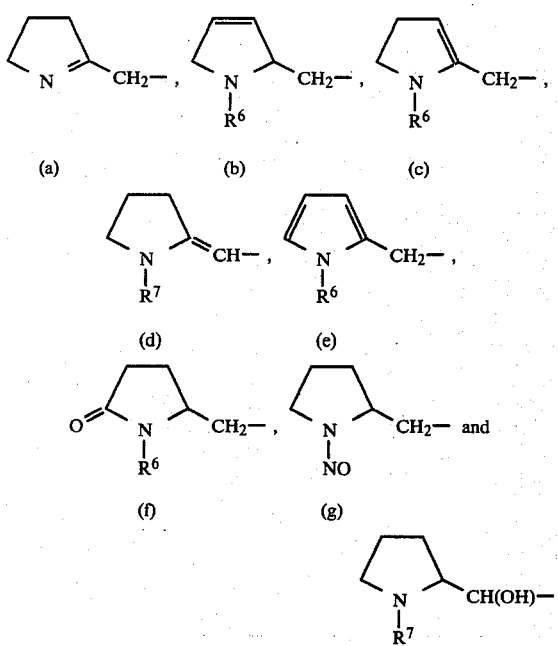

R[6] represents a hydrogen atom (—H), straight-chain or branched aliphatic or alicyclic hydrocarbyl, cycloalkylalkyl or optionally-substituted aralkyl group; and R[7] represents straight-chain or branched aliphatic or alicyclic hydrocarbyl, cycloalkylalkyl or optionally-substituted aralkyl;

is reduced and, where appropriate, subsequently N-alkylated or N-debenzylated and/or functionalized; an obtained free base is optionally conventionally converted into an acid-addition salt or vice versa; any obtained acid-addition salt is optionally converted into another in the usual well-established manner; or (b) a 2-benzylpyrrolidine or formula III

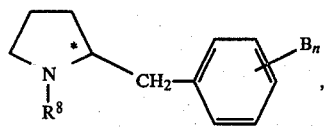

wherein
R[8] denotes a hydrogen atom (—H), straight-chain or branched aliphatic or alicyclic hydrocarbyl or cycloalkylalkyl;
B denotes a hydrogen atom or a precursor of a functional group and
n denotes a whole number from 1 to 4, preferably 1 or 2, and particularly 1;
is functionalized and, where appropriate, subsequently N-alkylated or N-debenzylated; the obtained free base or its acid-addition salts are readily converted into one another in the usual well-established manner; or
(c) an N-acyl-2-benzylpyrrolidine of formula IV

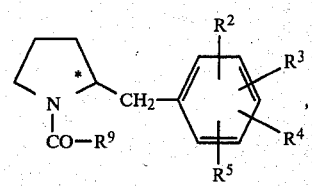

wherein
R[2], R[3], R[4] and R[5] are the same or different and denote a hydrogen atom, halo, alkyl, hydroxyl, alkoxy, optionally-substituted amino, or optionally-substituted phenyl; and
R[9] denotes straight-chain or branched aliphatic or alicyclic hydrocarbyl, cycloalkylalkyl, optionally-substituted phenyl or optionally-substituted phenylalkyl;
is reduced and, where appropriate, subsequently functionalized and/or N-alkylated or N-debenzylated; the obtained base or its acid-addition salts are optionally converted into one another in the usual manner.

Reduction of substituted 2-benzylpyrrolidines of formulae IIa through IIe and IIg is preferably effected with hydrogen in an organic solvent (such as is known to the artisan for hydrogenation reactions), for example ethanol, methanol, cyclohexane, isopropanol and dimethylformamide, in the presence of (i.e. in contact with) a metal catalyst, e.g. platinum, platinum on activated charcoal or Raney nickel, at a pressure within the range of about 1 to 500 atmospheres and at a temperature around room temperature, for example from 0° to 50° C. The reduction of compounds of formulae IIa, IIc and IId is alternatively effected in the form of their acid-addition salts in aqueous-alcoholic solution with sodium borohydride in a manner familiar to the skilled man (cf. "Enamines: Synthesis, Structure and Reactions", edited by A. Gilbert Cook, page 185 ff, MARCEL DEKKER, New York and London, 1969). The reduction of compounds IIf is effected with lithium aluminum hydride in an inert solvent, such as an ether, e.g. diethyl ether, tetrahydrofuran, dioxan, 1,2-dimethoxyethane or diethyleneglycol diethyl ether, at a temperature between 0° C. and the boiling temperature of the solvent, preferably between 20° and 70° C. The reduction of the compounds IIg is alternatively effected by reaction with hydrogen halogenides, preferably hydrogen chloride, in inert solvents, e.g. benzene (cp. Synthesis, 1976, 540–41). The reduction of the compounds IIh is effected with hydrogen iodide in, preferably, polar solvent, such as acetic acid, water, at temperatures between 80° and 150° C., preferably at the reflux temperature of the solvent, optionally in the presence of red phosphorus.

The compounds of formula IIa:

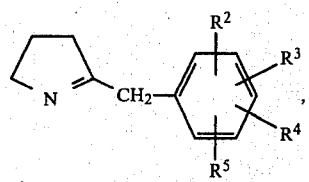

in which each of R[2], R[3], R[4] and R[5] has its previously-ascribed meaning,
are obtained along the lines of, or according to, processes described in the literature. For example, ω- chlorobutyronitrile is reacted with an appropriately-substituted benzylmagnesium halide, preferably those substituted by chloro and/or alkoxy, in a known solvent, such as an ether, e.g. diethyl ether or tetrahydrofuran, or an aromatic hydrocarbon, e.g. benzene, toluene or xylene, at a temperature between 20° and 160° C. to obtain the corresponding substituted $\Delta^1$-pyrroline. Compounds of formula IIa are alternatively obtained according to I. Felner et al. [*Helv. Chim. Acta* 53 (1970)754] or M. Roth et al. [*Helv. Chim. Acta* 54 (1971) 710] by reacting 2-thiopyrrolidinone V with an appropriately-substituted α-bromophenylacetic acid ester VI to obtain the corresponding thiolactam ether VII; subsequent sulfide contraction (yielding the enamino ester VIII) is followed by hydrolysis and decarboxylation, as is reflected in the following reaction scheme:

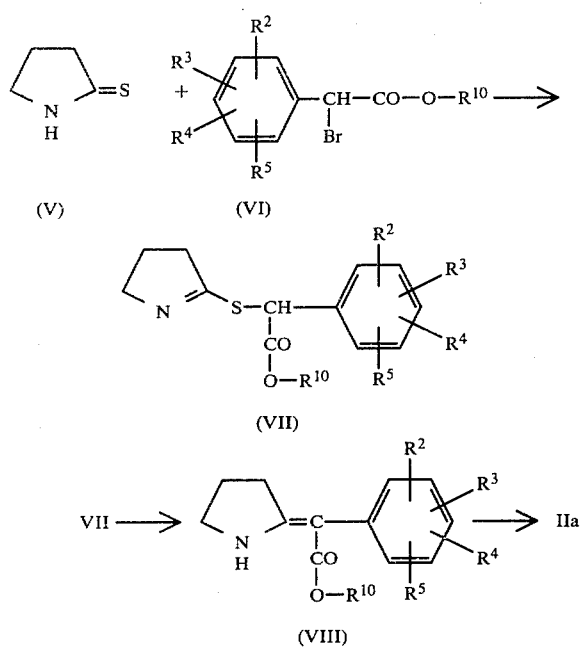

in which
each of $R^2$, $R^3$, $R^4$ and $R^5$ has its previously-ascribed meaning, and
$R^{10}$ denotes alkyl with from 1 to 5 carbon atoms.

Suitable sulfur scavengers (thiophilics) are, e.g., triphenylphosphine, triethylphosphite and tributylphosphine; for the hydrolysis and subsequent decarboxylation, strong acids, e.g. hydrochloric acid and trifluoroacetic acid, are predominantly used.

Compounds of general formula IIa are also prepared in analogy with the process described in German Offenlegungsschrift (Published Specification) 1,470,168 from 2-alkoxy-1-pyrrolines and an appropriate benzylmagnesium halide.

Compounds of formula IIa are also synthesized by reacting a benzylidene compound IX:

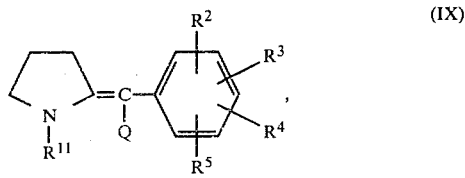

wherein
each of $R^2$, $R^3$, $R^4$ and $R^5$ has its previously-ascribed meaning;
$R^{11}$ represents a hydrogen atom (—H); and
Q represents a —CN group,
with a strong acid, e.g. concentrated hydrochloric acid. Benzylidene compounds IX, in which $R^{11}$ represents a hydrogen atom, are produced, for example, according to the process described by T. Kametani et al. [*J. Chem. Soc., Perkin* I 1976, 389; *Heterocycles*, 3 (1975), 691]. [In other compounds of formula IX $R^{11}$ is, optionally, one of the meanings of $R^7$, and Q is, e.g., —CO—O—$R^{10}$.]

Compounds of formulae IIb and IIc are prepared according to the procedure of C. M. Wong et al. [*Can. J. Chem.* 47 (1969) 2421], M. Salmón et al. [*C.A.* 73 (1970) 14604 u] or S. Oida et al. [*Chem. Pharm. Bull.* 17 (1969) 1405]. Compounds of formula IIb (with $R^6$ having a meaning different from hydrogen, e.g. a hydrocarbon radical or optionally-substituted aralkyl) are obtained by known methods, e.g. by alkylation or aralkylation.

Compounds IId are prepared according to any of various processes. For example, they are obtained by reacting a pyrrolidine X with a phenyl-acetic acid ester XI to obtain the corresponding benzylidene compound IX; hydrolysis and decarboxylation of the latter results in the corresponding compound IId according to the reaction scheme:

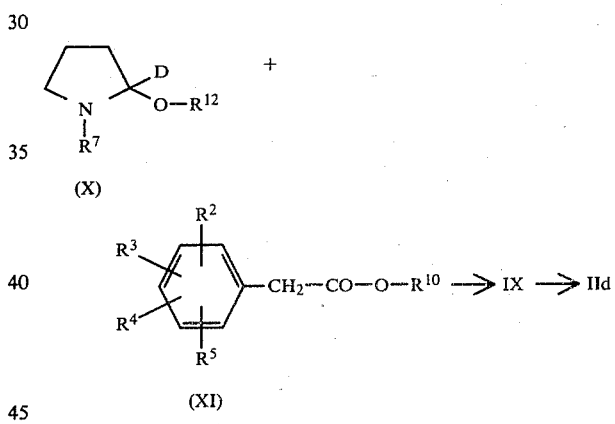

wherein
D denotes —O—$R^{13}$ or

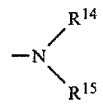

$R^{11}$ (in IX) has the meaning of $R^7$;
each of $R^{12}$, $R^{13}$, $R^{14}$ and $R^{15}$ is, independently, alkyl with from 1 to 5 carbon atoms, preferably methyl;
$R^{15}$ is alternatively cycloalkyl with from 3 to 6 ring carbon atoms or optionally-substituted phenyl;
D and O—$R^{12}$ together optionally denote alkylenedioxy with up to 4, preferably 2, carbon atoms;
Q (in IX) denotes —CO—O—$R^{10}$; and
each of $R^2$, $R^3$, $R^4$, $R^5$, $R^7$ and $R^{10}$ has its previously-ascribed meaning;
following work by N. P. Kostyuchenko et al. (*Khim. Geterotsikl. Soedin.* 1974, 1212). Analogously, compounds of the formula IId are obtained from a pyrrolidine K and an appropriate phenylacetonitrile via the corresponding benzylidene compound IX, in which Q represents CN.

Pyrrolidines X are obtained by reacting a salt of formula XII with alkali-metal alcoholate, such as sodium methylate or ethylate, in a suitable solvent [following the procedure of H. Bredereck et al., *Chem. Ber.* 97 (1964) 3081; *Chem. Ber.* 98 (1965) 1078]. Preferred solvents [when preparing pyrrolidines X in which D denotes —O—$R^{13}$] are alcohols of the formula $R^{13}$—OH, in which $R^{13}$ has its previously-ascribed meaning; preferred solvents [when preparing pyrrolidines X in which D denotes —$N(R^{14})R^{15}$] are inert solvents, such as benzenes, e.g. benzene, and ethers, e.g. diethylether.

The reaction of a pyrrolidine x with an acetic acid ester XI or an appropriate acetonitrile is generally carried out at a temperature of from 20° to 150° C., preferably between 40° and 100° C., without or preferably with addition of inert organic solvents, such as aliphatic hydrocarbon, e.g. petroleum ether, light petroleum or ligroin; cycloaliphatic hydrocarbon, e.g. cyclohexane; or aromatic hydrocarbon, e.g. benzene, toluene or xylene. Hydrolysis and simultaneous decarboxylation of the esters or of the appropriate acetonitriles are effected through the action of mineral acid, such as hydrochloric acid or hydrobromic acid, preferably of concentrated hydrochloric acid, at a temperature between room temperature (20° C.) and 120° C., preferably through heating the appropriate solution under reflux until the cessation of evolution of $CO_2$. Enamines IId formed from esters IX or the appropriate acetonitriles are relatively unstable compounds and are generally immediately further processed, i.e. reduced to yield corresponding compounds according to the invention. On account of their stability and their ready accessibility, as well as by reason of the instability of enamines IId, esters IX or the appropriate nitriles represent interesting and valuable intermediates for the preparation of 2-benzylpyrrolidines Ia according to the invention.

Compounds IId are alternatively obtained according to a further process by reacting a pyrrolinium salt XII with a phenylacetic acid derivative XIII in contact with a strong base to produce a benzylidene compound IX; hydrolysis and decarboxylation of the latter results in the corresponding compound IId according to the reaction scheme:

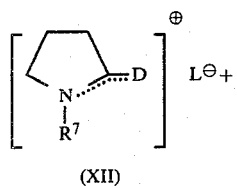

(XII)

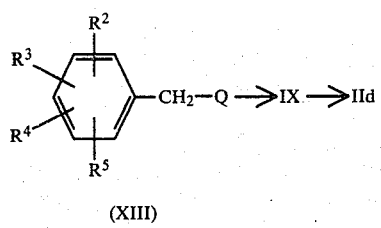

(XIII)

in which
each of $R^2$, $R^3$, $R^4$, $R^5$, $R^7$ and D has its previously-ascribed meaning;
Q represents —CN or —CO—O—$R^{10}$;
$R^{10}$ has its previously-ascribed meaning; and $L^\ominus$ stands for an equivalent of an anion of an organic or inorganic acid.

The reaction of a pyrrolinium salt XII with a phenylacetic acid derivative XIII is generally effected in presence of strong base, such as a solution of alkali-metal alcoholate, for example sodium methylate, potassium methylate, potassium propylate, sodium isopropylate, potassium butylate, potassium tert.-butylate and potassium tert.-pentylate, particularly sodium ethylate, without addition of further solvents at a temperature of from 20° to 150° C., preferably from 80° to 100° C. Where appropriate, the reaction is conducted while passing an inert gas, such as nitrogen, through the reaction mixture in order to remove any volatile amine wich may be formed. The reaction is, however, optionally effected with addition of inert solvent, such as an alcohol, e.g. methanol, ethanol, propanol, isopropanol, butanol or pentanol; a tertiary nitrogen base, e.g. pyridine; or a hydrocarbon, e.g. benzene, to the reaction mixture. The hydrolysis and decarboxylation of the benzylidene compound IX are effected analogously to the corresponding previously-described processes.

Preparation of salts XII is effected, e.g., in analogy with the procedure of H. Bredereck et al. (*Chem. Ber.* 1964, 3081) by reacting an appropriate N-substituted 2-pyrrolidinone wth an alkylating agent, such as diethyl sulfate, methyl iodide or, preferably, dimethyl sulfate, in inert solvent at a temperature from room temperature up to 120° C., but preferably without solvent at a temperature of around 80° C., and [when D in salt XII represents —$N(R^{14})R^{15}$] subsequently reacting the obtained product with an amine $HN(R^{14})R^{15}$ or (when D represents —$N(R^{14})R^{15}$) by reacting an appropriate pyrrolidinone with an inorganic acid chloride, such as phosphoryl chloride ($POCl_3$) or phosgene, and subsequently reacting the resulting product with an amine $HN(R^{14})R^{15}$ in an inert solvent, such as benzene, at a temperature between 0° and 100° C., preferably between 40° and 80° C.

Compounds IId are also obtained by reaction of an appropriate 2-pyrrolidinone or its derivative X with a substituted (advantageously disubstituted and preferably monosubstituted) benzylmagnesium halide, e.g. a nuclearly-substituted benzylmagnesium chloride, under conventional reaction conditions for Grignard reactions (cf. Houben-Weyl, Vol. 13/20, p. 53 ff.).

Compounds IId (in which at least one of the substituents $R^2$, $R^2$, $R^4$ and $R^5$ represents nitro) are alternatively obtained by reacting a pyrrolidine X with a toluene

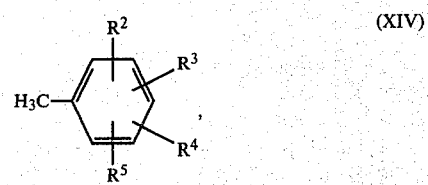

in which at least one of the substituents $R^2$, $R^3$, $R^4$ or $R^5$ represents nitro. The reaction is generally effected at a temperature of from 20° to 150° C., preferably between 40° and 100° C., in a reaction mixture without or preferably, with inert organic solvent, such as aliphatic hydrocarbon, e.g. petroleum ether, light petroleum or ligroin; cycloaliphatic hydrocarbon, e.g. cyclohexane; or aromatic hydrocarbon, e.g. benzene, toluene or xylene.

Compounds IId (in which at least one of the substituents $R^2$, $R^3$, $R^4$ or $R^5$ represents nitro) are also obtained by reacting a pyrrolinium salt XII with a toluene XIV (in which at least one of the substituents $R^2$, $R^3$, $R^4$ or $R^5$ represents nitro) in a reaction mixture containing strong base, such as alkali-metal alcoholate. Suitable alkali-metal alcoholates are, for example, sodium methylate, potassium methylate, potassium propylate, sodium isopropylate, potassium butylate, potassium tert.-butylate, potassium tert.-butylate and, in particular, sodium ethylate. The reaction is carried out at a temperature of from 20° to 150° C., preferably at from 80° to 100° C. Where appropriate, the reaction is performed while passing an inert gas, such as nitrogen, through the reaction mixture to remove any volatile amine which is formed. The reaction is effected either without addition of further solvent or with addition of inert solvent, such as alcohol, e.g. methanol, ethanol, propanol, isopropanol, butanol or pentanol; tertiary nitrogen base, e.g. pyridine; or hydrocarbon, e.g. benzene or toluene, to the reaction mixture.

Compounds IIe are obtained, for example, according to a process described in German Offenlegungsschrift 1,470,387. 2-(p-methoxybenzyl)pyrrole is referred to in C.A. 63, 5582g and C.A. 73, 14604u. 2-(p-chlorobenzyl)pyrrole is obtained by reducing 2-(p-chlorobenzoyl)pyrrole [described in *J. Chem.* (London) 1964, 2573]. Other substituted benzylpyrroles IIe are analogously obtained.

Compounds IIf are obtained, for example, by reacting a nitrile XIII with a succinic acid dialkylester, e.g. succinic acid diethylester, in a reaction mixture with alkali metal alcoholate, e.g. sodium ethylate, subsequently hydrolyzing and decarboxylating analogously to procedures of French Pat. No. 1,503,260 to obtain an appropriately-substituted phenyl-levulinic acid, converting the latter into the corresponding oxime and amine and subsequently cyclizing analogously to the procedure of Yakugaku Zasshi, 86 (1966) 1213–1216. Thus-prepared starting compounds IIf (with $R^6$ denoting a hydrogen atom) are optionally subsequently alkylated according to known established processes to yield compounds IIf wherein $R^6$ is alkyl, cycloalkyl, optionally-substituted aralkyl or cycloalkylalkyl.

The starting compounds IIg are obtained, for example, by lithiation of 1-nitrosopyrrolidine and subsequent reaction with corresponding benzyl halide, preferably bromide or iodide, in accordance with the process described in *Synthesis*, 1976, 540–41.

The starting compounds IIh are obtained, for example, by Grignard reaction of corresponding 2-formylpyrrolidines with correspondingly-substituted phenyl magnesium halides, preferably bromides, and usual working up in accordance with the process described in *Tetrahedron Letters* 28 (1976) 2437–40. They are obtained, alternatively, by reduction of correspondingly-substituted [pyrrolidinyl-(2)] phenyl ketones with lithium aluminum hydride. The pyrrolidinyl phenyl ketones are obtained in accordance with the process described *Helv. Chim. Acta*, 50 (1967) 2520.

Functionalization of a 2-benzylpyrrolidine III or, where appropriate, subsequent functionalization of a substituted benzylpyrrolidine Ia obtained by reduction is effected in a manner depending on the nature of the ultimately-desired substituent on the phenyl ring.

Nitro is introduced on the phenyl ring, for example, by nitration with nitric acid, nitric acid/sulfuric acid, potassium nitrate/sulfuric acid or alkyl nitrate at a temperature of from −20° to +50° C., preferably from −20° to +30° C. From a starting compound III (wherein B denotes a hydrogen atom and n = 1) and end product (wherein each of $R^2$, $R^4$ and $R^5$ denotes a hydrogen atom and $R^3$ denotes a p-positioned —$NO_2$ group) is thus obtained. Under severer conditions, dinitro compounds are formed; each of $R^4$ and $R^5$ denotes a hydrogen atom and each of $R^2$ and $R^3$ denotes a nitro group.

Amino is introduced on the phenyl ring by reducing (with hydrogen on a suitable catalyst, such as Pt, Pt/C, Pd, Pd/C or Raney Ni, in a customary solvent, such as an alcohol or cyclohexane) the —$NO_2$ group(s) of a corresponding nitro compound. From a starting compound III [wherein B denotes one or two —$NO_2$ groups and n = 1 (or 2)] an end product [wherein each of $R^4$ and $R^5$ denotes a hydrogen atom and $R^2$ and/or $R^3$ denotes an $NH_2$ group] is thus obtained.

Halogen atoms, in particular chlorine and bromine atoms, are introduced on the phenyl ring in the conventional manner through nuclear halogenation. Suitable catalysts for nuclear halogenation are iron, iron(III) chloride or bromide, aluminum chloride or bromide, tin tetrachloride or iodine; the reaction is carried out without solvent, in inert solvent or, where appropriate, in glacial acetic acid without catalyst at a temperature between 0° and 20° C.

Hydroxyl groups are introduced on the phenyl ring through ether splitting of an appropriate alkoxy group. In starting compounds III, B then denotes alkoxy, preferably methoxy, and n = 1 to 4, preferably 2, and particularly 1.

Ether splitting is carried out, e.g., by boiling a compound III wherein B is alkoxy with hydriodic acid, hydrobromic acid or a mixture of hydrogen bromide/glacial acetic acid or, alternatively, by reacting such compound III with boron tribromide in an inert solvent, such as chloroform or dichloromethane, at a temperature of from −20° to 20° C.

Etherification is effected, for example, by reacting a compound of formula III (wherein B is —OH) with an alkyl halide in a reaction mixture containing an equivalent amount of alkali-metal alcoholate, e.g. sodium ethylate.

Debenzylation, e.g., of a compound I or Ia (wherein $R^1$ is benzyl) is effected by hydrogenolysis in reaction medium containing catalyst, preferably palladium on charcoal, in solvent, such as methanol, ethanol, benzene or cyclohexane, at a temperature of from 0° to 50° C., preferably at room temperature, and under a hydrogen pressure of from 1 to 300, preferably from 1 to 5, atmospheres.

N-alkylation is carried out according to conventional methods. By a suitable choice of reaction conditions, the reaction is so conducted that either N-alkyl, N-cycloalkyl, N-aralkyl or N-cycloalkylalkyl derivatives are obtained, or corresponding alkylpyrrolidinium compounds are obtained. When N-alkylation is conducted to obtain a free-base derivative, the N-alkylation is carried out with a corresponding alkylating agent, such as an alkyl halide, alkyl sulfonates, e.g. tosylate, or alkyl sulfates, in inert solvent, such as a ketone, e.g. acetone or methyl ethyl ketone; or an alcohol, such as methanol, ethanol or isopropanol, or without solvent, with an auxiliary base, such as sodium carbonate, potassium carbonate or triethylamine, at a temperature of from about 20° to 100° C. When the N-alkylation is to obtain N-quaternization, i.e. to yield alkylpyrrolidinium compounds, reaction is carried out in a solvent, such as acetone, methyl ethyl ketone, ethyl acetate or an alcohol, with an alkylating agent, such as an alkyl halide, alkyl tosylate or alkyl sulfate, at a temperature of from 20° to 100° C.

When appropriate, subsequent acylation of free hydroxyl or of amino groups is conventionally carried out according to established methods, e.g. by reaction with an appropriate acid anhydride or halide (cf., inter alia, Houben-Weyl, Vol. 8, p. 543 ff. and 655 ff.). Splitting off an acyl group with liberation of hydroxyl or amino is conventionally effected in the usual manner by hydrolysis, e.g. by reaction with a suitable base, such as a sodium hydroxide or potassium hydroxide solution.

An acid-addition salt is obtained by dissolving a free base of formula I or Ia in a suitable solvent, e.g. acetone, water or lower aliphatic alcohol (ethanol, isopropanol) which contains the desired acid or to which the desired acid is subsequently added. The salt is obtained by filtration, precipitation with a non-solvent for the addition salt or by evaporation of the solvent.

An acid-addition salt, e.g. a hydrochloride, is converted into the corresponding free base by neutralization with aqueous sodium hydroxide or potassium hydroxide; the free base is then obtained by solvent extraction with a suitable water-immiscible solvent, such as chloroform, dichloromethane, diethyl ether, benzene, toluene or cyclohexane. The free base is alternatively obtained by neutralization of an acid-addition salt with sodium methylate in methanol and conventional isolation of the base according to known processes. An acid-addition salt is also converted into the corresponding free base by ion exchange. Basic anion exchange resin, e.g. Amberlite ® IRA 400, is used for this purpose.

Racemate or racemic mixture splitting is carried out according to well-established procedure, e.g. by addition of an optically-active acid, such as mandelic acid, tartaric acid, camphor-sulfonic acid or dibenzoyltartaric acid, recrystallization of the precipitated salt until constancy of the specific rotation is obtained and liberation of the optically-active base with alkali solution. From the mother liquor of the first precipitated salt, the other enantiomer is analogously obtained.

Reduction of an N-acyl-2-benzylpyrrolidine of formula IV is effected according to known methods, e.g. by reaction with a complex metal hydride as reducing agent in an anhydrous organic solvent and hydrolytic working up. Suitable reducing agents include lithium aluminum hydride, sodium dihydro-bis-(2-methoxyethoxy)aluminate and mixtures thereof. Suitable solvents include inert anhydrous ethers, such as diethyl ether, tetrahydrofuran, dioxan, 1,2-dimethoxyethane or diethyleneglycol diethyl ether, and aromatic hydrocarbons, such as benzene or toluene, or mixtures of such solvents. The temperature of the reaction is not critical and may vary within wide limits, for example from 0° to 100° C. Usually it is most expedient to carry out the reaction at the reflux temperature of the reaction mixture. The reaction duration is dependent on the reaction temperature and varies between about 1 hour and 24 hours. When conducted under reflux, the reaction is normally concluded within from 3 to 4 hours. The reactants may be used in equivalent amounts, but an excess of the reducing agent is preferred. Following the reaction with the reducing agent, the reaction product is worked up by treatment of the reaction mixture with an aqueous medium, such as water, dilute aqueous inorganic acid or base or other aqueous media. The product is isolated as free base or as acid-addition salt by adjusting the pH value.

Preparing starting compounds of formula III is effected in accordance with the publications referred to in "background". They are, alternatively, obtained by reaction of 1-phenyl-2,5-dibromopentane with corresponding amines $R^1$—$NH_2$ in analogy to the process described by F. F. Blicke and B. A. Brown [J. Org. Chem., 26 (1961) 3685, particularly pages 3686 and 3689]. 2-Benzyl-pyrrolidine is also obtained by reduction of 2-benzyl-1-nitrosopyrrolidine.

Preparing starting compounds of formula IV is likewise effected according to known methods, for example by acylation of an appropriate benzylpyrrolidine with a carboxylic acid halide, such as Cl—CO—$R^9$ (wherein $R^9$ is as previously defined) or a carboxylic acid anhydride in an inert solvent, such as benzene, toluene, cyclohexane, chloroform or dichloromethane, in a reaction mixture containing an auxiliary base, such as pyridine or triethylamine, at a temperature between 0° and 80° C. Suitable carboxylic acid halides are, for example, acetyl chloride, propionyl chloride, butyryl chloride, pivaloyl chloride, cyclopropylcarbonyl chloride, cyclobutylcarbonyl chloride, benzoyl chloride and phenyl acetyl chloride.

PHARMACOLOGY

The pharmacological properties, e.g. central stimulation, reserpine antagonism, analgesic action, anticataleptic effect and anti-hypertensive activity, of the compounds according to the invention are clearly demonstrable on albino mice and albino rats.

In the subsequent Tables, each investigated compound is assigned an identification number according to the following enumeration:

| Compound No. | Name of Compound |
|---|---|
| 1 | 2-(3-methoxybenzyl)-1-methylpyrrolidine |
| 2 | 2-(4-chlorobenzyl)-1-methylpyrrolidine |
| 3 | 2-(4-aminobenzyl)-1-methylpyrrolidine |
| 4 | 2-(2-methoxybenzyl)-1-methylpyrrolidine |
| 5 | 2-(4-chlorobenzyl)-1-isopropylpyrrolidine |
| 6 | 2-(4-chlorobenzyl)pyrrolidine |
| 7 | 2-(3-hydroxybenzyl)-1-methylpyrrolidine |
| 8 | 2-(4-fluorobenzyl)-1-methylpyrrolidine |
| 9 | 2-(4-bromobenzyl)-1-methylpyrrolidine |
| 10 | 2-(4-chlorobenzyl)-1-cyclopropylmethylpyrrolidine |
| 11 | 2-(4-methoxybenzyl)pyrrolidine |
| 12 | 2-(4-hydroxybenzyl)-1-methylpyrrolidine |
| 13 | 1-methyl-2-(4-nitrobenzyl)pyrrolidine |
| 14 | 2-(3,4-dimethoxybenzyl)-1-methylpyrrolidine |
| 15 | 2-(2,4-dichlorobenzyl)-1-methylpyrrolidine |
| 16 | 1-methyl-2-(3-methylbenzyl)pyrrolidine |
| 17 | 2-(3-chlorobenzyl)-1-methylpyrrolidine |
| 18 | 2-(4-methoxybenzyl)-1-methylpyrrolidine |
| 19 | 2-(3,4-dihydroxybenzyl)-1-methylpyrrolidine |
| 20 | 1-allyl-2-(4-chlorobenzyl)pyrrolidine |
| 21 | 1-methyl-2-(3,4,5-trimethoxybenzyl)pyrrolidine |
| 22 | 2-(4-chlorobenzyl)-1-hexylpyrrolidine |
| 23 | 2-(2-chlorobenzyl)-1-methylpyrrolidine |
| 24 | 1-methyl-2-(3,4,5-trihydroxybenzyl)pyrrolidine |

Compounds according to the invention are distinguished by central stimulation, which is reflected in an increase of vigilance and excitability; in rarer cases, also in mild promotion of motor activity. The results of behavior investigations on the albino mouse are reproduced in Table I.

TABLE I

| Increase of vigilance and excitability | | | Additional increase of activity | | |
| --- | --- | --- | --- | --- | --- |
| Compound No. | mg/kg orally | Intensity | Compound No. | mg/kg orally | Intensity |
| 1 | 5 | ++ | 5 | 25 | + |
| 2 | 5 | ++ | 10 | 100 | + |
| 3 | 5 | ++ | 22 | 100 | + |
| 4 | 5 | ++ | 9 | 200 | + |
| 5 | 5 | ++ | | | |
| 6 | 10 | +(+) | | | |
| 7 | 25 | + | | | |
| 8 | 5 | +(+) | | | |
| 9 | 25 | + | | | |
| 10 | 25 | + | | | |
| 11 | 25 | + | | | |
| 12 | 25 | + | | | |
| 13 | 50 | + | | | |
| 14 | 50 | + | | | |
| 15 | 50 | + | | | |
| 16 | 50 | (+) | | | |
| 17 | 50 | (+) | | | |
| 18 | 50 | (+) | | | |
| 19 | 100 | (+) | | | |
| 20 | 50 | (+) | | | |
| 21 | 50 | (+) | | | |
| 22 | 30 | (+) | | | |
| 23 | 5 | (+)* | | | |

Intensity scale:
++ greatly increased
+(+) very distinctly increased
+ distinctly increased
(+) mildly increased
*decrease from 50 mg/kg orally Among the compounds according to the invention, some have a particularly strong reserpine-antagonistic activity. This antagonism is demonstrable in the case of prophylactic and therapeutic administration. Table II presents the $ED_{50}$ values according to investigations on the albino mouse.

TABLE II

(a) Prophylactic administration to the mouse

| Compound No. | Abolition of ptosis [mg/kg orally] | Promotion of drive [mg/kg orally] |
| --- | --- | --- |
| 3 | 10 | 12 |
| 6 | 28 | 10 |
| 1 | 25 | 25 |
| 19 | 50 | 50 |
| 16 | 75 | 50 |
| 7 | 80 | 55 |
| 15 | >100 | 50 |
| 5 | (100)* | 65 |
| 10 | (100)* | 70 |
| 9 | 150 | |

(b) Therapeutic administration to the mouse

| Compound No. | Abolition of ptosis [mg/kg orally] | Promotion of drive [mg/kg orally] |
| --- | --- | --- |
| 3 | 18 | 37 |
| 7 | 25 | 30 |
| 1 | 50 | 75 |
| 5 | 75 | 75 |
| 16 | 25 | (100)* |
| 11 | 90 | 90 |
| 4 | 80 | 100 |
| 17 | (75)* | 75 |
| 13 | (100)* | 60 |
| 10 | (100)* | 85 |

( )*values: $ED^{30}$

For compounds according to the invention, analogesic effects are evidenced in various analgesic models on the albino mouse. In Table III the $ED_{50}$ values (calculated from the dose effect curves) are presented.

TABLE III

| (a) Hot plate test | | (b) Tail-flick test | |
| --- | --- | --- | --- |
| Compound No. | [mg/kg orally] | Compound No. | [mg/kg orally] |
| 4 | 2.0 | 5 | 25 |
| 6 | 2.5 | 3 | 50 |
| 22 | 3.5 | 9 | 50 |
| 18 | 5 | 19 | 50 |
| 2 | 5 | 22 | 70 |
| 17 | 20 | 11 | 80 |
| 13 | 25 | | |
| 11 | 25 | (c) Writhing test (acetic acid) | |
| 14 | 35 | Compound No. | [mg/kg orally] |
| 3 | 50 | 5 | 35 |
| 19 | 50 | 18 | 45 |
| 23 | 50 | 3 | 50 |
| 21 | 50 | 4 | 60 |

Compounds according to the invention have prophylactic activity against the formation of a catalepsy caused by haloperidol. In Table IV the $ED_{50}$ values according to investigations on the albino mouse are reproduced.

TABLE IV

| Compound No. | [mg/kg orally] |
| --- | --- |
| 6 | 7 |
| 2 | 24 |
| 21 | 25 |
| 5 | 25-50 |
| 20 | 65 |
| 3 | 80 |

Compounds according to the invention cause a reduction of blood pressure in the anaesthetized normotonic albino rat. Table V presents data reflecting the maximum lowering of blood pressure [in mm of Hg] in the range of the first 5 minutes and 60 minutes after intravenous administration of a dose of 50 μmoles/kg.

TABLE V

| Compound No. | Lowering of blood pressure [mm of Hg] Max. [5 min. after administration | 60 min. after administration |
| --- | --- | --- |
| 19 | 35 | 28** |
| 23 | 51 | 39 |
| 7 | 40 | 32 |
| 4 | 40 | 38 |
| 3 | 38 | 19 |
| 6 | 36 | 18 |
| 16 | 28 | 10 |
| 2 | 27 | 15 |
| 1 | 26 | 15 |
| 24 | 23 | 22 |
| 5 | 15 | 12 |

**administration of only 10 μmoles/kg

The determination of the pharmacological properties was effected according to the following methods:

1. Behavior

To observe the behavior of albino mice, in each instance 5 animals were kept in a Makrolon cage, Type II. A comparative assessment, vis-a-vis untreated controls, was made. Vigilance and increase of motor activity were assessed from the behavior of undisturbed mice; the increased excitability was assessed from reaction to outer stimuli, such as noise and touch, in comparison with the reaction of the control animals.

2. Reserpine antagonism

Subcutaneous administration of 2 mg/kg of reserpine causes ptosis ("Reserpine Drive Inhibition") [Sulser, Bichel, Brodie, 1961 Med. Exp. 5, 454] in albino mice in the course of several hours; also, the normal movement activity of the animal (drive) [Domenjoz and Theobald (1959), Arch. Int. Pharmacodyn. 120/450] is considerably inhibited. The intensity of both symptoms was graded by a rating scale: 0-1-2-3, by which the degree of the effect (from no effect to complete ptosis, and from no inhibition to complete inhibition of drive) is reflected. These experiments were conducted both under prophylactic and under therapeutic administration of the test substances. The substances tested antagonized the symptoms in a dose-dependent manner. The $ED_{50}$ of the antagonistic effect was evaluated in comparison with the daily control.

3. Analgesia (a) Hot-plate test: female albino mice were placed on a 50° C. hot plate, and the reaction time until paws were licked was recorded with a stopwatch. Normal values lie in the range of 7 to 8 seconds. The substances tested caused delayed reaction to the heat stimulus, i.e. a reduced sensitivity to heat pain. The dose which prolonged the reaction time by 50% was determined. Literature: Eddy, N. B., and Leimbach, D. (1953) J. Pharmacol. Exp. Ther. 107, 385.

(b) Tail-flick test [D'Amour, F. E. and Smith, D. L., (1941) J. Pharmacol. Exp. Ther. 72, 74]: a thermal pain was applied to female albino mice on the tail root with a focused heat ray, and the time until the tail is drawn away was recorded with a stopwatch. Normally, the time is in the range of from 4 to 5 seconds. The substances caused delayed reaction to the thermal pain, i.e. a reduced reaction to thermal pain. The dose which prolonged the reaction time by 50% was determined.

(c) Writhing test (acetic acid writhing [L. Joulou, M.-C. Bardone, R. Ducrot, B. Laffargue and G. Loiseua in "Neuro-Psycho-Pharmacology", Ed. H. Brill et al., *Exerpta Medica Foundation Internat. Congress Series No. 129*, 293 to 303 (1967)]): intrapertioneal injection of 0.2 ml/20 g of mouse body weight (v/v) of a 0.75% acetic acid solution induces (in albino mice) a typical syndrome, called "writhing", proceeding over the body with dorsal flection. The writhes (occurring in the course of the first half hour after administration) were counted over a period of from 5 to 20 minutes after administration. The substances tested caused a decrease in the number of writhing syndromes. The dose which reduces the number of writhes by 50% with reference to the daily control was determined.

4. Haloperidol antagonism

Subcutaneous administration of haloperidol (7.5 mg/kg) causes catalepsy in albino mice. The cataleptic behavior of the animals was tested by placing the animals on a wire cradle bridge for 30 seconds [L. Joulou, M.-C. Bardone, R. Ducrot, b. Laffargue and G. Loiseau in "Neuro-Psycho-Pharmacology", Ed. H. Brill et al., *Exerpta Medica Foundation* Internat. Congress Series No. 129, 293 to 303 (1967)]. The substances tested prevented, in a dose-dependent manner, the occurrence of catalepsy after administration of haloperidol. The dose which inhibited the occurrence of catalepsy in 50% of the animals was determined.

5. Blood pressure determinations

The substances were administered intravenously to normotone albino rats (Sprague Dawley; male) which had been anaesthetized with chloralose (80 mg/kg intraperitoneally). The blood pressure measurement was effected in the A. carotis dexter by means of a Statham pressure recorder; the measurement of the heart frequency was effected with an EKA pulse rate meter. The body temperature was kept constant to 37.5°±0.2° C. by warming with an incandescent lamp which was controlled via a rectal temperature sensor. Recordation was effected continuously over one hour p.a. The maximum of the effect within the first 5 minutes and of the effect after 60 minutes were determined.

EXAMPLES

The following Examples explain the invention more fully without restricting it. The abbreviation, m.p., denotes melting point; b.p. denotes boiling point; conc. denotes concentrated; tert. denotes tertiary; and decomp. denotes decomposition. Temperature are in °C.

EXAMPLE 1

2-(4-chlorobenzylidene)-1-methylpyrrolidine (a) Prepare a Grignard solution from 9.66 grams (g) of p-chlorobenzyl chloride and 1.46 g of magnesium filings in 100 milliters (ml) of diethyl ether. To this solution add dropwise (with stirring) a solution of 8.65 g of 2,2-diethoxy-1-methylpyrrolidine in 50 ml of diethyl ether while the resulting reaction mixture remains boiling. Keep the mixture at the boil for a further 1 hour before adding 10 ml of saturated ammonium chloride solution dropwise and then collecting the ether solution. Extract the obtained residue three times with, in each case, 100 ml of diethyl ether; combine the ether solutions; dry the combined extract over magnesium sulfate and concentrate it. Add 5 ml of methanol to the resulting oily residue to crystallize it and thus obtain 2.9 g (28% of theory) of the title compound (m.p. 63°).

(b) According to the method described in Example (22b), obtain from 15 g of 2-(α-cyano-4-chlorobenzylidene)-1-methylpyrrolidine 8.8 g (77% of theory) of the title compound in the form of crystals (having a tendency to decompose) of m.p. 60° to 63°.

EXAMPLE 2

2-(4-chlorobenzyl)-1-methylpyrrolidine (a) Dissolve 28 g of 2-(p-chlorobenzylidene)-1-methylpyrrolidine in 250 ml of methanol and hydrogenate the thus-obtained solution with Raney nickel as catalyst. Filter the catalyst from the hydrogenated product and then concentrate the filtrate to obtain 22.7 g of the title compound having a boiling point of 75° at 0.005 millimeters (mm) of Hg (yield: 81% of theory). The picrate (from ethanol) melts at 149°.

React the title base with an equivalent amount of each corresponding acid to obtain the following salts:

| | |
|---|---|
| hibenzate: | colorless viscous oil |
| citrate: | colorless oil |
| fumarate: | yellowish oil |
| benzoate: | yellow viscous oil |
| maleate: | light-yellow oil |
| oxalate: | pink oil |
| embonate: | yellow viscous oil |

(b) Boil 40 g of 2-(α-ethoxycarbonyl-4-chlorobenzylidene)-1-methylpyrrolidine and 150 ml of conc. hydrochloric acid under reflux until the cessation of evolution of carbon dioxide. Cool the thus-obtained reaction mixture and then render it alkaline with 10% strength solution of sodium hydroxide before extracting the resulting product with 5×70 ml of diethyl ether. After drying over sodium sulfate, concentrate the ether extract to a solid residue. Hydrogenate the solid residue in 550 ml of ethanol with Pt/hydrogen to obtain 27.6 g of the title compound having a boiling point of 75° at 0.005 mm of Hg.

EXAMPLE 3

2-dimethylamino-1-methyl-1-pyrrolinium-methylsulfate

Add dropwise, with stirring, 22.5 g of 2-methoxy-1-methyl-1-pyrrolinium-methylsulfate to a solution of 6.76 g of dimethylamine in 45 ml of benzene and then boil the obtained admixture under reflux for 1 hour. Separate off the resulting heavy phase; extract it twice by shaking it out with diethyl ether and then free the extract from solvent residue in a vacuum to obtain 19.4 g (81.4% of theory) of title compound as reddish brown oil.

EXAMPLE 4

2-(α-ethoxycarbonyl-4-chlorobenzylidene)-1-methyl-pyrrolidine

Add [dropwise, with stirring, at 100° (bath temperature), in a stream of nitrogen] a solution of 9.6 g of sodium in 200 ml of ethanol to a mixture of 99 g of 2-dimethylamino-1-methyl-1-pyrrolinium-methylsulfate and 65 g of 4-chlorophenylacetic acid ethyl ester. Remove the alcohol from the reaction mixture by the stream of nitrogen. Continue stirring for a further 30 minutes at 100°; cool the reaction mixture; add 200 ml of water to the cooled reaction mixture; and then extract it with 5×100 ml of diethyl ether. Combine the ether extracts, dry the combined extracts over sodium sulfate, concentrate them and then remove a little excess 4-chlorophenylacetic acid ethyl ester by heating under a high vacuum to obtain a yield [86 g (94% of theory)] of crude title compound having a m.p. of 71°.

EXAMPLE 5

1-isopropyl-2-methoxy-1-pyrrolinium-methylsulfate

Stir 89.6 g of 1-isopropylpyrrolidinone-2 and 88.9 g of dimethylsulfate for 3 hours at 80°. Extract the reaction mixture 5 times with, in each case, 50 ml of diethyl ether and dry the obtained red oil under a high vacuum to obtain 167.2 g (94% of theory) of title compound.

Thin-layer chromatography: layer silica gel neutral; flow agent: chloroform/methanol 9:1, $R_F$ value 0.30; color reagent: iodine vapor

EXAMPLE 6

1-isopropyl-2-dimethylamino-1-pyrrolinium-methylsulfate

Add dropwise, with stirring, 161 g of 1-isopropyl-2-methoxy-1-pyrrolinium-methylsulfate to a solution of 43.8 g of dimethylamine in 283 ml of benzene. Subsequently, boil the resulting reaction mixture under reflux for 1.5 hours; separate off the heavy phase and wash it 4 times with, in each case, 50 ml of diethyl ether. Dry the washed product under a high vacuum to obtain 154 g (91% of theory) of the title compound as reddish oil.

EXAMPLE 7

2-(α-ethoxycarbonyl-4-chlorobenzylidene)-1-isopropyl-pyrrolidine

Add [dropwise, with stirring, at from 90°–100°, in a stream of nitrogen] a solution of 5.1 g of sodium in 100 ml of ethanol to a mixture of 32 g of 4-chlorophenylacetic acid ethyl ester and 59.13 g of 1-isopropyl-2-dimethylamino-1-pyrrolinium-methylsulfate. After completion of the addition, continue stirring for a further 30 minutes; then cool and take up with water ($\approx 100$ ml) and diethyl ether ($\approx 150$ ml). Collect the organic phase, extract the aqueous phase once again with diethyl ether, combine the ether extracts, dry and concentrate them to obtain a yield [45.6 g (92% of theory)] of crude title compound; recrystallize 5 g from ethanol/water to obtain 4.2 g of product with a m.p. of 70° to 71°.

EXAMPLE 8

2-(4-chlorobenzyl)-1-isopropylpyrrolidine

Boil 40.6 g of 2-(α-ethoxycarbonyl-4-chlorobenzylidene)-1-isopropylpyrrolidine and 115 ml of conc. hydrochloric acid under reflux until evolution of carbon dioxide ceases. Alkalize the resulting reaction mixture with 250 ml of 6 N sodium hydroxide solution before extracting with 400 ml of diethyl ether, dry the ether phase over sodium sulfate and concentrate it. Dissolve thus-obtained residue in 250 ml of ethanol, and hydrogenate the resulting solution with platinum/hydrogen. Then filter off the catalyst and distil off the solvent before distilling the product under a high vacuum to obtain a yield [21.8 g (70% of theory)] of title compound and having a b.p. of 75° at $7 \cdot 10^{-3}$ mm of Hg.

Convert a sample into the picrate which has a m.p. of 126° to 127° (from ethanol).

EXAMPLE 9

2-(4-chlorobenzyl)pyrroline-1

(a) Add (dropwise, with stirring) a solution of 83 g of 4-chlorobutyronitrile in 300 ml of diethyl ether to a Grignard solution (prepared from 22.3 g of magnesium filings and 147 g of 4-chlorobenzyl chloride in 250 ml of diethyl ether). Keep the resulting mixture at the boil for 1 hour. Then distil off the ether and, simultaneously, add 700 ml of xylene dropwise to the batch before boiling it under reflux (bath temp. 170°) for 1 hour, then allowing it to cool and subsequently adding (slowly, with stirring) 150 ml of saturated ammonium chloride solution to it. Filter off produced magnesium salts and wash them well with xylene and diethyl ether. Extract the basic components from the combined organic components with 15% strength hydrochloric acid (250+150 ml), wash the obtained aqueous phase with 100 ml of diethyl ether and alkalize (with ice cooling) with 6 N sodium hydroxide solution. Extract the oil phase (which separates) with diethyl ether and, after drying thus-obtained extract over sodium sulfate, distil it to obtain 22.3 g (16% of theory) of title compound having a b.p. of 109° to 113° at 0.01 mm of Hg. The free base is unstable. The m.p. of the perchlorate (from ethanol): 196° to 198°. The m.p. of the hydrochloride (from methanol/diethyl ether): 176° to 178°.

(b) Boil 80 g of 2-(α-cyano-4-chlorobenzylidene)pyrrolidine and 200 ml of concentrated hydrochloric acid under reflux for 2.5 hours. After cooling, alkalize the refluxed reaction mixture with 6 N sodium hydroxide solution. Then extract the alkalized mixture 3 times with, in each case, 200 ml of diethyl ether. Dry the combined ether extracts over sodium sulfate and then concentrate them to a yellowish oil. Distil the yellowish oil under a vacuum to obtain the title compound [yield 53.0 g (74% of theory)] with a b.p. of 88° to 90° at 0.004 mm of Hg.

EXAMPLE 10

2-(4-chlorobenzyl)pyrrolidine

Hydrogenate 28.5 g of 2-(4-chlorobenzyl)pyrroline-1 in 300 ml of ethanol with Raney nickel/hydrogen. After removal of solvent and catalyst, distil the resulting product under a high vacuum to obtain 23.0 g (80% of theory) of title compound having a b.p. of 70° to 72° at 0.001 mm of Hg. The m.p. of the hydrochloride (from methanol/diethyl ether): 190° to 192°.

EXAMPLE 11

2-(N-methyl-N-phenyl)amino-1-methyl-1-pyrrolinium-perchlorate

Add 21.5 g of phosphorus oxytrichloride dropwise to 19.8 g of 1-methylpyrrolidinone-2 in such a manner that the temperature of the resulting admixture does not rise above 40°. After a further 15 minutes, add 16.5 g of N-methylaniline dropwise to the thus-prepared reaction mixture at 60°. Then add 20 ml of 2 N hydrochloric acid and 450 ml of ice water thereto. Add 21.6 g of sodium perchlorate to the obtained solution to precipitate 38.6 g (95% of theory) of title compound as colorless crystals. Recrystallize from isopropanol to obtain a product with a m.p. of 96.5° to 97°.

EXAMPLE 12

2-(α-methoxycarbonyl-3,4-dimethoxybenzylidene)-1-methylpyrrolidine

Add a solution of 0.46 g of sodium in 5 ml of methanol dropwise to a mixture of 5.8 g of the title compound of Example 11 and 4.5 g of homoveratric acid ethyl ester in 15 ml of pyridine. Stir the resulting reaction mixture for 2 hours at 60°, and then distil pyridine and alcohol off under a vacuum before extracting the oily residue first with water and subsequently with petroleum ether. Chromatograph thus-extracted residue on a silica gel column with chloroform/methanol (19:1) to obtain eluate with an $R_F$ value 0.76. Concentrate the eluate to obtain a yield (10.5% of theory) of the title compound in the form of an oil.

EXAMPLE 13

2-(α-ethoxycarbonyl-3,4-dimethoxybenzylidene)-1-methylpyrrolidine

Add (dropwise at room temperature with stirring) a solution of 0.46 g of sodium in 10 ml of ethanol to a mixture of 5.8 g of title compound of Example 11 and 4.5 g of homoveratric acid ethyl ester in 20 ml of ethanol. Boil the resulting reaction mixture under reflux for 2 hours. Remove alcohol and methylaniline under a high vacuum and purify the residue by column chromatography on silica gel. Collect the title compound (having an $R_F$ value 0.72) in the flow agent, chloroform/methanol (19:1), in a yield of 0.9 g (15% of theory).

EXAMPLE 14

3,4-dimethoxybenzylidene-1-methylpyrrolidine

Boil 12.4 g of 2-(α-methoxycarbonyl-3,4-dimethoxybenzylidene)-1-methylpyrrolidine for 15 minutes with 40 ml of conc. hydrochloric acid. Cool the resulting reaction mixture before rendering it alkaline with sodium hydroxide solution. Filter off the thus-produced precipitate and recrystallize it from ethanol/water 2:1 to obtain 3.2 g (32% of theory) of title compound having a m.p. of 72°.

EXAMPLE 15

3,4-dimethoxybenzyl-1-methylpyrrolidine

Dissolve 12.2 g of 3,4-dimethoxybenzylidene-1-methylpyrrolidine in methanol and reduce the pyrrolidine in the thus-obtained solution with Raney nickel/hydrogen. Filter off the catalyst and distil off the methanol before distilling the residue to obtain 9.6 g (79%) of the title compound with a b.p. of 90° at 0.005 mm of Hg. The m.p. of the picrate (from ethanol) is 105° to 106°.

EXAMPLE 16

2-(α-tert.-butoxycarbonyl-4-methoxybenzyl)mercaptopyrroline-1

Boil 18.4 g of thiopyrrolidinone-2 and 56 g of α-bromo-4-methoxyphenylacetic acid tert.-butyl ester for 3 hours in 300 ml of dichloromethane. Cool the obtained reaction product and then wash the organic phase with (in each case) 100 ml of 25% potassium carbonate solution and saturated sodium chloride solution. Dry the thus-washed material over sodium sulfate and then concentrate to a yellowish oil. Crystallize the yellowish oil from 500 ml of n-hexane with activated charcoal to obtain a yield [52.2 g (90% of theory)] of colorless crystals having a m.p. of 66° to 67°.

EXAMPLE 17

2-(α-tert.-butoxycarbonyl-4-methoxybenzylidene)pyrrolidine

Stir 25 g of 2-(α-tert.-butoxycarbonyl-4-methoxybenzyl)mercaptopyrroline-1 (title compound of Example 16) and 1.0 g of potassiumm tert.-butylate in 160 ml of phosphorous acid trimethyl ester and 24 ml of dimethylsulfoxide under nitrogen at 100°. After 65 hours, remove the solvents under a vacuum, dissolve the residue in 200 ml of diethyl ether and then sequentially extract the ether phase (in each case once) with (in each case 100 ml of) water, 1 N hydrochloric acid, dilute sodium carbonate solution and saturated sodium chloride solution. After drying and concentrating, recrystallize the residue from n-hexane to obtain 13.2 g (59% of theory) of the title compound (m.p. 98° to 100°).

EXAMPLE 18

2-(4-methoxybenzyl)pyrrolidine

Add 80 ml of trifluoroacetic acid to 15 g of the title compound of Example 17 with ice cooling, and stir the produced reaction mixture for 2 hours at room temperature. Distil off the acid under a vacuum. Dissolve the resulting residue in 250 ml of diethyl ether and wash the thus-prepared solution with almost saturated cold sodium carbonate solution (150 ml) and saturated sodium chloride solution. Dry the washed solution over sodium sulfate and distil off the ether before dissolving the residue in 300 ml of ethanol and reducing it with Raney nickel/hydrogen. Concentrate the reduced solution to an oil and distil the oil under a vacuum to obtain 7.5 g (76% of theory) of the title compound (b.p. 88° to 90° at 0.008 mm of Hg).

The hydrochloride (from ethanol/ether) melts at 141° to 142°.

EXAMPLE 19

α-bromo-3,4-dimethoxyphenylacetic acid tert.-butyl ester

Heat 58.2 g of homoveratric acid tert.-butyl ester and 43.3 g of N-bromosuccinimide under reflux for 2 hours in 1.3 liters of carbon tetrachloride under irradiation with a 500-watt immersion lamp. After cooling, filter out the succinimide and concentrate the filtrate. Dissolve the resulting concentrate in 250 ml of diethyl ether and extract the produced solution by shaking it with water. Free the ether solution from the solvent under a vacuum to obtain 50 g (66% of theory) of the title compound as a non-distillable oil.

EXAMPLE 20

2-(α-tert.-butoxycarbonyl-3,4-dimethoxybenzyl)mercaptopyrroline-1

Boil 15 g of thiopyrrolidinone-2 and 49 g of α-bromo-3,4-dimethoxyphenylacetic acid tert.-butyl ester for 1 hour in 200 ml of dichloromethane under reflux. Wash the refluxed mixture with (in each case 100 ml of) ice-cold potassium carbonate solution and saturated sodium chloride solution. After drying the washed mixture over sodium sulfate, concentrate it to 47.2 g (90% of theory) of the title compound in the form of a non-distillable oil.

EXAMPLE 21

2-(α-tert.-butoxycarbonyl-3,4-dimethoxybenzylidene)-pyrrolidine

Stir 35 g of 2-(tert.-butoxycarbonyl-3,4-dimethoxybenzyl)mercaptopyrroline-1 and 1.8 g of potassium tert.-butylate in 160 ml of phosphorous acid trimethyl ester and 23 ml of dimethylsulfoxide for 24 hours at 100° under nitrogen. Distil off the solvents under a high vacuum. Dissolve the residue in 300 ml of diethyl ether and then sequentially extract the ether phase (in each case once) with (in each case 100 ml of) 1 N hydrochloric acid, dilute sodium carbonate solution and saturated sodium chloride solution. Dry the ether phase over sodium sulfate and distil off the ether to obtain 29.5 g (93% of theory) of the title compound as a light-brown, non-distillable oil.

EXAMPLE 22

2-(3,4-dimethoxybenzyl)pyrroline-1

(a) Dissolve 29.3 g of the title compound of Example 21 in 120 ml of trifluoroacetic acid, with ice cooling, and stir the prepared solution at room temperature for 2 hours. Distil off the acid and dissolve the residue in 500 ml of diethyl ether, extract the ether solution with (in each case 100 ml of) cold saturated sodium carbonate solution and saturated sodium chloride solution. After drying the ether solution over sodium sulfate, concentrate it to 14.6 g (72% of theory) of the title compound as a yellowish oil.

The picrate (from ethanol) melts at 139° to 141°.

(b) Boil 24.4 g of 2-(α-cyano-3,4-dimethoxybenzylidene)pyrrolidine with 60 ml of concentrated hydrochloric acid under reflux for 15 minutes. After cooling the refluxed mixture, alkalize it with 6 N sodium hydroxide solution and then extract the base with diethyl ether. Distil off the solvent to obtain 16.0 g (73% of theory) of the title compound as a yellowish oil.

EXAMPLE 23

2-(3,4-dimethoxybenzyl)pyrrolidine (a) Hydrogenate 13.1 g of 2-(3,4-dimethoxybenzyl)-pyrroline-1 in 300 ml of ethanol with Raney nickel/hydrogen. Filter the catalyst, concentrate the filtrate, and distil the resulting residue to obtain 3.6 g of title compound (b.p. 116° at 0.007 mm of Hg). Purify further by column chromatography on silica gel to collect a product with an $R_F$ value of 0.36 (flow agent chloroform/methanol 4:1, carrier silica gel) in a yield of 504 mg (5% of theory).

A sample of the picrate (from ethanol) melts at 180° to 181°; a sample of the hydrogen fumarate (from ethanol) melts at 165° to 166°.

(b) Hydrogenate 11.7 g of 1-benzyl-2-(3,4-dimethoxybenzyl)pyrrolidine in ethanol with 6.5 g of palladium/activated charcoal (10% strength)/hydrogen. Free the product from solvent and catalyst, and then distil it under a high vacuum. Purify via the picrate to obtain a yield of 3.2 g (38.5% of theory).

EXAMPLE 24

2-dimethylamino-1-benzyl-1-pyrrolinium-1-methylsulfate

Heat 35 g of 1-benzylpyrrolidinone-2 and 25.2 g of dimethylsulfate at 80° for 8 hours. Extract the resulting reaction mixture several times with diethyl ether and benzene, and then add the thus-produced viscous oil dropwise, with stirring, to a solution of 20 ml of dimethylamine in 80 ml of benzene. Boil the resulting admixture under reflux for 1 hour, collect the heavy phase and extract it 3 times with diethyl ether to obtain a yield of 35.4 g (55% of theory) of title compound as a viscous oil.

EXAMPLE 25

1-benzyl-2-(α-ethoxycarbonyl-3,4-dimethoxybenzylidene)pyrrolidine

Add (dropwise at 90°, with stirring, in a stream of nitrogen) a solution of 2.6 g of sodium in 50 ml of ethanol to 34.5 g of 2-dimethylamino-1-benzyl-1-pyrroliniummethylsulfate and 19.7 g of homoveratric acid ethyl ester. Keep the resulting reaction mixture at this temperature for a further 30 minutes and then distribute it between water and diethyl ether. Dry the ether solution over sodium sulfate and then concentrate it to obtain a yield [32.2 g (96% of theory)] of title compound.

EXAMPLE 26

1-benzyl-2-(3,4-dimethoxybenzylidene)pyrrolidine

Boil 31.5 g of 1-benzyl-2-(α-ethoxycarbonyl-3,4-dimethoxybenzylidene)pyrrolidine under reflux with 75 ml of conc. hydrochloric acid until carbon dioxide ceases to evolve. After cooling, alkalize the thus-prepared reaction mixture with sodium hydroxide solution. Recrystallize the formed precipitate from ethanol to obtain a yield [11.3 g (44% of theory)] of title compound (m.p. 105°).

EXAMPLE 27

1-benzyl-2-(3,4-dimethoxyphenyl)pyrrolidine

Dissolve 3 g of 1-benzyl-2-(3,4-dimethoxybenzylidene)pyrrolidine in ethanol and hydrogenate with platinum/hydrogen. Distil the hydrogenated product under a vacuum to obtain 2.3 g (77% of theory) of title compound (b.p. 173° at 0.007 mm of Hg).

The picrate (from ethanol) melts at 153°.

EXAMPLE 28

2-(α-ethoxycarbonyl-4-nitrobenzylidene)-1-methylpyrrolidine

Boil 50 g of 4-nitrophenylacetic acid ethyl ester and 41.4 g of 2,2-diethoxy-1-methylpyrrolidine under reflux for 3 hours in 250 ml of benzene. Distil off the benzene before recrystallizing the resulting residue from diethyl ether/petroleum ether to obtain the title compound at a yield of 52.6 g (77% of theory) in the form of red crystals of m.p. 82° to 83°.

EXAMPLE 29

1-methyl-2-(4-nitrobenzylidene)pyrrolidine (a) Boil 11 g of 2-(α-ethoxycarbonyl-4-nitrobenzylidene)-1-methylpyrrolidine in 100 ml of conc. hydrochloric acid until carbon dioxide ceases to evolve. Alkalize the thus-prepared reaction mixture with sodium hydroxide solution to produce a red precipitate (8.7 g). Filter off the precipitate and recrystallize a sample from ethanol to obtain the title compound (m.p. 133° to 134°).

(b) Add a solution of 2.35 g of potassium tert. butylate in 15 ml of tert. butanol and 10 ml of dimethylformamide dropwise at 130° to a mixture of 5.0 g of 2-dimethylamino-1-methyl-1-pyrrolinium methylsulfate and 2.2 g of 4-nitrotoluene in 15 ml of dimethylformamide. Stir the thus-prepared reaction mixture at this temperature for 2 hours. Allow the mixture to cool, add water to it and then extract it several times with chloroform. Combine and then concentrate the chloroform extracts. Distil off a slight excess of 4-nitrotoluene under a high vacuum and recrystallize the produced residue from 10 ml of ethanol to obtain 0.8 g of title compound.

EXAMPLE 30

2-(4-aminobenzyl)-1-methylpyrrolidine (a) Reduce 8.5 g of 1-methyl-2-(4-nitrobenzylidene)-pyrrolidine in ethanol with platinum/hydrogen. Remove the catalyst and solvent and recrystallize from n-hexane to obtain 3.6 g (49% of theory) of title compound (m.p. 59° to 61°).

m.p. of the hydrobromide (from ethanol/ether): 193° to 196°.

m.p. of the dihydrobromide (from ethanol/diethyl ether): 267° to 270°.

m.p. of the dihydrochloride (from ethanol/diethyl ether): 244° (decomp.)

(b) Hydrogenate 18 g of 2-(4-nitrobenzyl)-1-methylpyrrolidine in ethanol with 300 mg of platinum dioxide/hydrogen. Filter the catalyst from the reaction mixture, concentrate the latter and recrystallize the thus-produced residue from n-hexane to obtain the title compound at a yield of 12.7 g (82% of theory).

EXAMPLE 31

2-(α-ethoxycarbonyl-benzylidene)-1-methylpyrrolidine

Add a solution of 6.9 g of sodium in 140 ml of ethanol dropwise at 90°, with stirring, in a stream of nitrogen, to 84 g of 2-dimethylamino-1-methyl-1-pyrrolinium-methylsulfate and 37.9 g of phenylacetic acid ethyl ester. Stir the thus-prepared reaction mixture for a further 30 minutes at 90° and then distribute it between water and diethyl ether (300 ml of each). Isolate the product from the ether phase and distil it to obtain a yield of 48 g (85% of theory) of title compound (b.p. 106° to 107° at 0.008 mm of Hg).

EXAMPLE 32

2-(α-ethoxycarbonyl-2-methoxybenzylidene)-1-methylpyrrolidine

Follow the method of working described in Example 31 to obtain 63.8 g (71% of theory) of the title compound (b.p. 134° to 137° at 0.005 mm of Hg) from 50 g of 2-methoxyphenylacetic acid ethyl ester, 83.4 g of 2-dimethylamino-1-methyl-1-pyrrolinium-methylsulfate and a solution of 8.1 g of sodium in 160 ml of ethanol.

EXAMPLE 33

2-(α-ethoxycarbonyl-3,4,5-trimethoxybenzylidene)-1-methylpyrrolidine

Follow the procedure of Example 31 to obtain 36.2 g of the title compound (m.p. 115° to 116°, recrystallized from cyclohexane) from 51.7 g of 2-dimethylamino-1-methyl-1-pyrrolinium-methylsulfate, 40.6 g of 3,4,5-trimethoxyphenylacetic acid ethyl ester and a solution of 5.0 g of sodium in 100 ml of ethanol.

EXAMPLE 34

2-(α-ethoxycarbonyl-4-methoxybenzylidene)-1-methylpyrrolidine

Follow the procedure of Example 31 to obtain 1 g (20% of theory) of the title compound (m.p. 81° to 82°) from 4.8 g of 2-dimethylamino-1-methyl-1-pyrrolinium-methylsulfate, 3.5 g of 4-methoxyphenylacetic acid ethyl ester and a solution of 0.46 g of sodium in 10 ml of ethanol.

EXAMPLE 35

2-(α-ethoxycarbonyl-2-chlorobenzylidene)-1-methylpyrrolidine

Follow the procedure of Example 31 to obtain 73.8 g (93% of theory) of the title compound (b.p. 129° to 0.008 mm of Hg) from 98.4 g of 2-dimethylamino-1-methyl-1-pyrrolinium-methylsulfate, 56.1 g of 2-chlorophenylacetic acid ethyl ester and a solution of 9.5 g of sodium in 190 ml of ethanol.

EXAMPLE 36

2-(α-ethoxycarbonyl-3-chlorobenzylidene)-1-methylpyrrolidine

Follow the procedure of Example 31 to obtain 70 g (90% of theory) of the title compound (b.p. 137° at 0.006 mm of Hg) from 91 g of 2-dimethylamino-1-methyl-1-pyrrolinium-methylsulfate, 55.1 g of 3-chlorophenylacetic acid ethyl ester and a solution of 8.8 g of sodium in 175 ml of ethanol.

EXAMPLE 37

2-(α-ethoxycarbonyl-4-bromobenzylidene)-1-methylpyrrolidine

Follow the procedure of Example 31 to obtain 62.4 g (87% of theory) of the title compound (b.p. 128° at 0.006 mm of Hg) from 54.3 g of 4-bromophenylacetic acid ethyl ester, 74.3 g of 2-dimethylamino-1-methyl-1-pyrrolinium-methylsulfate and a solution of 7.2 g of sodium in 145 ml of ethanol.

EXAMPLE 38

2-(α-ethoxycarbonyl-4-fluorobenzylidene)-1-methylpyrrolidine

Follow the procedure of Example 31 to obtain 1.7 g (36% of theory) of the title compound (m.p. 80°, purified by column chromatography on silica gel) from 4.8 g of 2-dimethylamino-1-methyl-1-pyrrolinium-methylsulfate, 3.3 g of 4-fluorophenylacetic acid ethyl ester and a solution of 0.46 g of sodium in 10 ml of ethanol.

EXAMPLE 39

2-benzyl-1-methylpyrrolidine

Follow the procedure of Example 2(b) to obtain 10.7 g of 2-benzyl-1-methylpyrrolidine (b.p. 44° to 48° at 0.005 mm of Hg) from 20 g of 2-(α-ethoxycarbonyl-benzylidene)-1-methylpyrrolidine.

EXAMPLE 40

2-(3-chlorobenzyl)-1-methylpyrrolidine

Follow the procedure of Example 2(b) to obtain 34 g (72% of theory) of the title compound [b.p. 81° at 0.007 mm of Hg; m.p. of the pictrate (from ethanol) 186°] from 62.5 g of 2-(α-ethoxycarbonyl-3-chlorobenzylidene)-1-methylpyrrolidine.

EXAMPLE 41

2-(2-chlorobenzyl)-1-methylpyrrolidine

Follow the procedure of Example 2(b) to obtain 35.6 g (78% of theory) of the title compound (b.p. 81° at 0.008 mm of Hg) from 61 g of 2-(α-ethoxycarbonyl-2-chlorobenzylidene)-1-methylpyrrolidine.

EXAMPLE 42

2-(4-bromobenzylidene)-1-methylpyrrolidine

Follow the procedure of Example 14 to obtain 28.3 g of the title compound [m.p. 83° to 84° (recrystallized from ethanol)] from 59.9 g of 2(α-ethoxycarbonyl-4-bromobenzylidene)-1-methylpyrrolidine.

EXAMPLE 43

2-(4-bromobenzyl)-1-methylpyrrolidine

Hydrogenate 21.5 g of 2-(4-bromobenzylidene)-1-methylpyrrolidine in 400 ml of ethanol with platinum on activated charcoal/hydrogen. Filter out the catalyst, concentrate the filtrate and distil the residue to obtain 18.5 g (85% of theory) of the title compound (b.p. 70° at 0.001 mm of Hg).

The picrate (from ethanol) melts at 140° to 142°.

EXAMPLE 44

2-(4-fluorobenzyl)-1-methylpyrrolidine

Follow the procedure of Example 2(b) [hydrogenation catalyst=platinum] to obtain 7.5 g of the title compound (b.p. 57° at 0.006 mm of Hg) from 20 g of 2-(α-ethoxycarbonyl-4-fluorobenzylidene)-1-methylpyrrolidine.

EXAMPLE 45

2-(2-methoxybenzyl)-1-methylpyrrolidine

Follow the procedure of Example 2(b) to obtain 22.3 g (54% of theory) of the title compound (b.p. 73° to 0.005 mm of Hg) from 55 g of 2-(α-ethoxycarbonyl-2-methoxybenzylidene)-1-methylpyrrolidine.

The picrate (from ethanol) melts at 144°.

EXAMPLE 46

2-(4-methoxybenzyl)-1-methylpyrrolidine (a) Follow the procedure of Example 2(b) to obtain 7 g (85% of theory) of the title compound from 11 g of 2-(α-ethoxycarbonyl-4-methoxybenzylidene)-1-methylpyrrolidine (hydrogenation catalyst=platinum; purification by column chromatography on silica gel).

The picrate (from ethanol) melts at 139°.

(b) Heat 0.8 g of 2-(60 -cyano-4-methoxybenzylidene)-1-methylpyrrolidine under reflux for 15 minutes in 12 ml of concentrated hydrochloric acid. Then add 30 ml of ice water thereto, alkalize with 6 N sodium hydroxide solution and extract the resulting base with diethyl ether. Distil off the solvent to obtain an oily residue (440 mg). Dissolve this oily residue in ethanol and hydrogenate it with platinum/hydrogen. Free the hydrogenated product from the catalyst and distil off the solvent to obtain 320 mg (45% of theory) of the title compound as a yellowish liquid of b.p. 79° at 0.005 mm of Hg.

EXAMPLE 47

1-methyl-2-(3,4,5-trimethoxybenzyl)pyrrolidine

Follow the procedure of Example 2(b) to obtain 15.2 g of the title compound (b.p. 118° at 0.006 mm of Hg) from 30.2 g of 2-(α-ethoxycarbonyl-3,4,5-trimethoxybenzylidene)-1-methylpyrrolidine (Hydrogenation catalyst: platinum).

The picrate (from ethanol) melts at 125°.

EXAMPLE 48

2-(3-methoxybenzyl)-1-methylpyrrolidine

Add a solution of 8.1 g of sodium in 160 ml of ethanol dropwise at 90°, with stirring, in a stream of nitrogen to 83.4 g of 2-dimethylamino-1-methyl-1-pyrrolinium-methylsulfate and 48.3 g of 3-methoxyphenylacetic acid ethyl ester. Stir the resulting reaction mixture for a further 30 minutes at 90° and then distribute the reaction mixture between 300 ml of water and 300 ml of diethyl ether. Concentrate the ether phase and boil the residue with conc. hydrochloric acid until carbon dioxide ceases to evolve. After cooling, alkalize the boiled residue with 6 N sodium hydroxide solution before extracting it with diethyl ether. Dry the ether extract over sodium sulfate; concentrate it, and reduce the concentrate in methanol with platinum/hydrogen. Separate the catalyst by filtration, concentrate the filtrate and distil to obtain a yield of 23.0 g (45% of theory) of title compound (b.p. 88° at 0.005 mm of Hg).

The picrate (from ethanol) melts at 166°.

EXAMPLE 49

2-(4-nitrobenzyl)-1-methylpyrrolidine

Dissolve 27.9 g of 2-benzyl-1-methylpyrrolidine in 130 ml of conc. sulfuric acid, and add 100 ml of conc. nitric acid dropwise at 0°, with stirring, to the resulting solution. Continue stirring for a further 30 minutes at room temperature. Pour the mixture into 1 liter of ice water and alkalize with sodium hydroxide solution, with cooling. Extract the thus-produced preparation 4 times with, in each case, 150 ml of diethyl ether. Dry the ether phase over sodium sulfate and concentrate it to a red oil to obtain the title compound at a yield of 33.8 g (96% of theory). The hydrogen fumarate (from isopropanol) melts at 145° to 146°.

EXAMPLE 50

2-(3-hydroxybenzyl)-1-methylpyrrolidine

Boil 10.5 g of 2-(3-methoxybenzyl)-1-methylpyrrolidine under reflux for 50 hours in a mixture of 60 ml of acetic acid and 60 ml of 48% strength hydrobromic acid. Pour the resulting reaction mixture onto ice, adjust its pH to 10 with 6 N sodium hydroxide solution and extract it 3 times with diethyl ether. Combine and dry the ether phase, distil off the solvent and distil the residue under a vacuum to obtain 7.95 g (79% of theory) of the title compound (b.p. 128° to 130° at 0.006 mm of Hg). The fumarate (from isopropanol) melts at 189° to 191°.

EXAMPLE 51

2-(4-hydroxybenzyl)-1-methylpyrrolidine

Boil 6.2 g of 2-(4-methoxybenzyl)-1-methylpyrrolidine under reflux for 24 hours in a mixture of 30 ml of acetic acid and 30 ml of 48% strength hydrobromic acid. Add a further 20 ml of acetic acid and 20 ml of hydrobromic acid to the refluxed mixture and continue boiling for a further 24 hours. Pour the mixture onto 400 ml of ice water before adjusting its pH to 10 with 6 N sodium hydroxide solution and then extracting it 4 times with, in each case, 50 ml of diethyl ether. Dry the combined ether extracts over sodium sulfate and distil off the solvent. Recrystallize the resulting residue from 25 ml of ethanol to obtain a yield (65% of theory) of the title compound (m.p. 161° to 162°).

EXAMPLE 52

2-(3,4-dihydroxybenzyl)-1-methylpyrrolidine

Boil 5.0 g of 2-(3,4-dimethoxybenzyl)-1-methylpyrrolidine under reflux for 41 hours in a mixture of 45 ml of acetic acid and 45 ml of 48% strength hydrobromic acid. Remove the bulk of the acid through distillation under a vacuum. Take up the thus-produced residue with ice water and alkalize the resulting admixture with aqueous sodium carbonate solution. Extract the base with diethyl ether for several hours, distil off the solvent to obtain 4.1 g of residue and convert the residue into the hydrochloride of the title compound with methanol/ethereal hydrochloric acid to obtain 3.4 g (67% of theory) of product (m.p. 188°).

EXAMPLE 53

2-(α-cyano-4-chlorobenzylidene)-1-methylpyrrolidine (a) Boil 22.7 g of 2,2-diethoxy-1-methylpyrrolidine, 19.8 g of 4-chlorobenzylcyanide and 90 ml of benzene for 1 hour under reflux and with stirring. Distil off the volatile constituents under a vacuum. After trituration with a little diethyl ether, filter off the residue to obtain 20.8 g (68% of theory) and the title compound (m.p. 71° to 72° from isopropanol).

(b) Follow the procedure of Example 60 to obtain 23 g (53% of theory) of the title compound (m.p. 70° to 72°) from 36 g of 2-methoxy-1-methylpyrrolinium-1-methylsulfate, 24 g of p-chlorobenzylcyanide and a solution of 6.1 g of sodium in 100 ml of ethanol.

EXAMPLE 54

2-(α-cyano-4-methoxybenzylidene)-1-methylpyrrolidine

Boil 30.0 g of 2,2-diethoxy-1-methylpyrrolidine, 25 g of 4-methoxybenzylcyanide and 150 ml of benzene under reflux for 4 hours. Concentrate the refluxed reaction product and distil the residue twice under a vacuum to obtain 30.6 g (79% of theory) of the title compound (b.p. 158° at 0.005 mm of Hg).

EXAMPLE 55

2-(3-methylbenzyl)-1-methylpyrrolidine

Prepare a Grignard solution from 103 g of 3-methylbenzyl chloride and 8 g of magnesium in 400 ml of diethyl ether. With stirring and boiling under reflux, add a solution of 126.9 g of 2,2-diethoxy-1-methylpyrrolidine dropwise to the Grignard solution. Keep the thus-prepared mixture at the boil for a further 1 hour before adding 130 ml of saturated ammonium chloride solution dropwise thereto. Then filter off the magnesium salts and dry the filtrate over sodium sulfate. Free the residue (31 g) from ether and then hydrogenate it with Raney nickel/hydrogen. Distil the hydrogenated product twice under a vacuum to obtain 16.2 g (13% of theory) of the title compound (b.p. 56° to 0.001 mm of Hg).

The picrate (from ethanol) melts at 135° to 137°.

EXAMPLE 56

2-(4-bromobenzyl)-1-methylpyrrolidine

Add 11.4 moles of bromine at room temperature to 2 g of 2-benzyl-1-methylpyrrolidine and 50 mg of iron powder. Allow the resulting mixture to stand for 2 hours before rendering it alkaline 1 N sodium hydroxide solution. Extract the base with diethyl ether. Distil the ether extract to obtain the title compound as almost-colorless liquid of b.p. 72° at 0.001 mm of Hg.

EXAMPLE 57

2-(4-chlorobenzyl)pyrrolidine

Heat 20 g of 2-(4-chlorobenzoyl)pyrrole, 15 g of hydrazine hydrate, 28 g of potassium hydroxide and 100 ml of diethylene glycol to 150° for 2 hours. Allow the mixture to cool. Dilute it with water to twice its volume. Add hydrochloric acid to it until its pH is about 3 before extracting it with diethyl ether. Free the organic phase from solvent to obtain 2-(4-chlorobenzyl)pyrrole as oil remaining behind. Dissolve the oil in 25 ml of ethanol, and add this solution dropwise to a boiling mixture of 150 ml of 20% strength hydrochloric acid and zinc amalgum (prepared from 100 g of zinc, 10 g of mercury chloride and 150 ml of 0.5 N hydrochloric acid). Then add a further 200 ml of 20% strength hydrochloric acid and 50 g of amalgam and boil the resulting reaction mixture for a further 4 hours. Allow the mixture to cool, filter it, extract the filtrate with ethyl acetate (5×200 ml), concentrate the organic solution, add 6 N sodium hydroxide solution to the concentrate until zinc salts therein dissolve, and then extract with diethyl ether. Concentrate the ether solution. Dissolve the oil remaining behind in 200 ml of ethanol and hydrogenate on Pt/C contact. Filter the catalyst from the hydrogenated product. Concentrate the filtrate and then distil the concentrate under a vacuum to obtain the title compound [b.p. 76° to 79° at 0.005 mm of Hg]. The hydrochloric melts at 190° to 192°.

EXAMPLE 58

2-(4-methoxybenzyl)pyrrolidine

Hydrogenate 3.3 g of 2-(p-methoxybenzyl)pyrroline-3 in 100 ml of ethanol on Pt/C contact. Free the hydrogenated solution from the catalyst and concentrate the separated solution to obtain the title compound as an oily residue. Treat the oily residue with ethanol/ethereal hydrochloric acid to obtain 2-(4-methoxybenzyl)pyrrolidine hydrochloride of m.p. 140° to 142° (ethanol/ether).

EXAMPLE 59

1-tert.-butyl-2-methoxy-1-pyrrolinium-methylsulfate

Stir 108.8 g of 1-tert.-butylpyrrolidinone-2 and 97.0 g of dimethylsulfate at 80° for 3 hours. Allow the resulting mixture to cool to 35° to 40°, with stirring. Add absolute diethyl ether to the cooled mixture and filter off 164.4 g (80% of theory) of the title compound (m.p. 57° to 62°) in the form of crystallized salt.

EXAMPLE 60

1-tert.-butyl-2-($\alpha$-cyano-4-chlorobenzylidene)pyrrolidine

Heat 56.8 g of 1-tert.-butyl-2-methoxy-1-pyrrolinium-methylsulfate and 30.3 g of 4-chlorobenzylcyanide to 80°. Add thereto (dropwise, within 2 hours, with stirring) a solution of 8.1 g of sodium in 160 ml of ethanol. After completion of the addition, boil the prepared admixture for a further 2 hours. Concentrate the boiled admixture and distil off (at $10^{-3}$ mm of Hg) the excess 4-chlorobenzylcyanide. Recrystallize the resulting residue from 170 ml of ethanol to obtain 11 g of the title compound. Concentrate the mother liquor to obtain a further 2.5 g (24% of theory) of the title compound in the form of light-brown crystals of m.p. 150° to 153°.

EXAMPLE 61

2-($\alpha$-ethoxycarbonyl-4-chlorobenzylidene)-1-methylpyrrolidine

Follow the procedure of Example 60 to obtain 20.1 g (77% of theory) of the title compound (b.p. 132° to 134° at 0.005 mm of Hg) from 30 g of 4-chlorophenylacetic acid ethyl ester and 36.1 g of 2-methoxy-1-methyl-1-pyrrolinium-methylsulfate and to recover 9.1 g of 4-chlorophenylacetic acid ester.

EXAMPLE 62

2-($\alpha$-cyano-4-chlorobenzylidene)pyrrolidine

Stir 106 g of 2-methoxypyrroline-1, 243.5 g of 4-chlorobenzylcyanide and 9 ml of triethylamine for 20 hours at 110°. After cooling, add 200 ml of diethyl ether thereto and filter off the formed precipitate (80.9 of the title compound). Distil off the solvent and the 4-chlorobenzylcyanide under a vacuum to obtain a further 42 g of the title compound (m.p. 135° to 137°) for a total yield of 122.9 g (52% of theory).

EXAMPLE 63

2-[(4-biphenylyl)cyanomethylene]pyrrolidine

Stir 32.7 g of 2-methoxypyrroline, 63.8 g of 4-phenylbenzylcyanide and 5 g of 1,5-diazabicyclo[5,4,0]undec-5-ene for 26 hours at 110°. After cooling, take up the mixture with 500 ml of diethyl ether. Filter the formed precipitate and recrystallize it from 400 ml of ethanol with activated charcoal to obtain 12.2 g (14% of theory) of the title compound (m.p. 168° to 170°).

EXAMPLE 64

1-methyl-2-(3,4,5-trihydroxybenzyl)pyrrolidine

Boil 3.6 g of 1-methyl-2-(3,4,5-trimethoxybenzyl)pyrrolidine, 30 ml of 48% strength hydrobromic acid and 30 ml of acetic acid under reflux for 9 hours. Then add a further 10 ml of hydrobromic acid and 10 ml of acetic acid to the prepared reaction mixture and continue boiling it for a further 3 hours. Subsequently, concentrate it to dryness and recrystallize the residue twice from methanol diethyl ether to obtain 2.56 g (61% of theory) of the hydrobromide of the title compound in the form of slightly pink crystals (m.p.: 168° to 171°).

EXAMPLE 65

2-(4-chlorobenzyl)-1-cyclopropylcarbonylpyrrolidine

Add (dropwise, at 0° to 8°) 5.2 g of cyclopropanecarboxylic acid chloride in 10 ml of dichloromethane to 10 g of 2-(4-chlorobenzyl)pyrrolidine and 6.2 g of triethylamine. Stir the thus-prepared reaction mixture for a further 2 hours at 0°. Add water thereto. Separate off the organic phase and extract it with dichloromethane. Combine the organic phases and wash them with dilute hydrochloric acid and sodium carbonate solution. Dry the washed material over sodium sulfate. Evaporate off the solvent from the dried material, and then distil the oily residue to obtain the title compound (8.85 g) in the form of oil (b.p. 135° to 137° at 0.005 mm Hg), which solidifies to a crystalline mass of m.p. 62° to 64°.

EXAMPLE 66

2-(4-chlorobenzyl)-1-cyclopropylmethylpyrrolidine

Dissolve 3.0 g of 2-(4-chlorobenzyl)-1-cyclopropylcarbonylpyrrolidine in 30 ml of tetrahydrofuran, and add the thus-prepared solution (dropwise, within 10 minutes at 0°, with stirring) to a suspension of 0.43 g of lithium aluminum hydride (=lithium hydrido-aluminate) in 10 ml of tetrahydrofuran. Subsequently, boil the resulting reaction mixture under reflux for 1 hour. After cooling, cautiously add 50 ml of water thereto and extract the product 3 times with, in each case, 30 ml of diethyl ether. Combine the ether solutions and wash the combined extract with saturated sodium chloride solution. Dry the washed ether phase over sodium sulfate, evaporate off the solvent and distil the residue twice under a vacuum to obtain 1.65 g (58% of theory) of the title compound (b.p. 108° at 0.006 mm of Hg).

EXAMPLE 67

1-allyl-2-(4-chlorobenzyl)pyrrolidine

Boil 5 g of 2-(4-chlorobenzyl)pyrrolidine, 3.53 g of anhydrous potassium carbonate, 3.4 g of allyl bromide and 50 ml of ethyl methyl ketone under reflux for 1 hour. Evaporate off the solvent. Take up the residue with 50 ml of water and extract 3 times with, in each case, 30 ml of diethyl ether. Combine the ether phases and dry them over sodium sulfate. Distil off the solvent from the combined ether extract and distil the resulting residue under a vacuum to obtain 5.12 g (85% of theory) of the title compound (b.p. 84° to 87° at 0.005 mm of Hg). m.p. of the picrate (from ethanol): 115° to 117°.

EXAMPLE 68

2-(4-chlorobenzyl)-1-(n-hexyl)pyrrolidine

Boil 5 g of 2-(4-chlorobenzyl)pyrrolidine, 3.53 g of anhydrous potassium carbonate, 4.6 g of 1-bromohexane and 50 ml of ethyl methyl ketone under reflux for 18 hours. Work up according to the procedure o Example 67 to obtain 5.82 g (81% of theory) of the title compound as a colorless liquid of b.p. 110° to 112° at 0.005 mm of Hg.

EXAMPLE 69

2-(3,4-diacetoxybenzyl)-1-methylpyrrolidine

Allow 3.25 g of 2-(3,4-dihydroxybenzyl)-1-methylpyrrolidine to stand for 24 hours in 30 ml of acetic anhydride/pyridine 1:1. Concentrate the resulting reaction mixture under a vacuum and distil off the residue to obtain 3.5 g (76% of theory) of the title compound in the form of a yellowish oil (b.p. 135° to 140° at 0.005 mm of Hg) which, on standing, solidifies to a crystalline mass of m.p. 44° to 45°.

EXAMPLE 70

2-(4-chlorobenzyl)-1,1-dimethylpyrrolidinium iodide

Add 3.72 g of methyl iodide dropwise, with stirring, to 5.5 g of 2-(4-chlorobenzyl)-1-methylpyrrolidine in 40 ml of acetone. Filter off the formed crystalline precipitate and recrystallize it twice from methanol/diethyl ether to obtain 6.9 g (75% of theory) of the title compound (m.p. 184° to 186°).

EXAMPLE 71

2-($\alpha$-ethoxycarbonyl-2,4-dichlorobenzylidene)-1-methylpyrroline

Follow the procedure of Example 4 to obtain 19 g (61% of theory) of the title compound as a reddish oil of b.p. 130° at 0.001 mm of Hg from 47.7 g of 2-dimethylamino-1-methyl-1-pyrrolinium methylsulfate and 23 g of 2,4-dichlorophenylacetic acid ethyl ester.

EXAMPLE 72

2-(2,4-dichlorobenzyl)-1-methylpyrrolidine

Follow the procedure of Example 2(b) to obtain 10.4 g (72% of theory) of the title compound as a colorless liquid of b.p. 91° at 0.005 mm of Hg from 18.5 g of 2-($\alpha$-ethoxycarbonyl-2,4-dichlorobenzylidene)-1-methylpyrrolidine. The picrate (from ethanol) melts at 174° to 176°.

EXAMPLE 73

(+)-2-(4-chlorobenzyl)-1-methylpyrrolidine

Add a solution of 27 g of dibenzoyl-L-tartaric acid in 200 ml of acetone to 15 g of 2-(4-chlorobenzyl)-1-methylpyrrolidine dissolved in 100 ml of acetone. Allow the resulting mixture to stand for 6 hours at room temperature and for 4 days at 0°. Filter off the precipitated crystals (8.5 g). Concentrate the filtrate somewhat and then allow the mixture to stand for a further 12 hours at 0°. Collect the further-precipitated crystals (4.53 g). Recrystallize the collected crystalline products from 100 ml of acetone and filter to obtain a total yield of 9.9 g of (+)-2-(4-chlorobenzyl)-1-methylpyrrolidine dibenzoyl tartrate, m.p. 117° to 120°, $[\alpha]_{589}^{20} = -64°$ (25 mg/ml in methanol). Shake 9.4 g of this salt with diethyl ether/sodium hydroxide solution until solution is complete. Dry the ether phase, evaporate off the solvent and distill the residue to obtain 2.73 g of the base, the title compound, b.p. 70° at 0.005 mm of Hg, $[\alpha]_{589}^{20} = +78.9°$ (25 mg/ml in methanol).

Isolate the laevo-rotatory enantiomer (with an optical purity of 15.8%, $[\alpha]_{589}^{20} = 12.5°$) from the mother liquor of the precipitated crystals.

EXAMPLE 74

2-(4-biphenylylmethyl)pyrrolidine

Boil 10 g of 2-(4-biphenylyl)cyanomethylenepyrrolidine for 30 minutes with 30 ml of concentrated hydrochloric acid. After cooling the thus-produced reaction mixture, alkalize it with 6 N sodium hydroxide solution and then extract it with diethyl ether. Distil off the solvent to obtain an oily residue. Dissolve the residue in 100 ml of ethanol and then hydrogenate it with platinum/hydrogen. Filter the hydrogenated product from the catalyst and distil off the solvent to obtain the title compound as a yellowish oil (4.8 g).

EXAMPLE 75

1-acetyl-2-benzylpyrrolidine

Follow the procedure of Example 65 to obtain 5.8 g of the title compound as a viscous oil from 6 g of 2-benzylpyrrolidine, 4.14 of triethylamine and 2.65 g of acetyl chloride.

EXAMPLE 76

1-acetyl-2-(4-nitrobenzyl)pyrrolidine

Dissolve 5.0 g of 1-acetyl-2-benzylpyrrolidine (at 0°) in 25 ml of concentrated sulfuric acid. At this temperature add (dropwise, with stirring) 20 ml of concentrated nitric acid to the thus-prepared solution. After warming the obtained reaction mixture to room temperature, pour it into 200 ml of ice water and extract it with diethyl ether. After drying over sodium sulfate, treat the extract with activated charcoal and then distil off the solvent to obtain the title compound as reddish oil.

EXAMPLE 77

1-acetyl-2-(4-aminobenzyl)pyrrolidine

Hydrogenate 3.3 g of 1-acetyl-2-(4-nitrobenzyl)pyrrolidine with platinum/hydrogen in ethanol. Filter the catalyst from the hydrogenated product and concentrate the filtrate to obtain the title compound as a yellowish liquid.

EXAMPLE 78

1-ethyl-2-(4-aminobenzyl)pyrrolidine

Follow the procedure of Example 66 to obtain 1.3 g (55% of theory) of the title compound as a viscous light-brown oil from 2.5 g of 1-acetyl-2-(4-aminobenzyl)pyrrolidine and 0.44 g of lithium aluminum hydride.

EXAMPLE 79

2-benzyl-1-cyclopropylcarbonylpyrrolidine

Follow the procedure of Example 65 to obtain 5.2 g of the title compound as an oil of b.p. 120° to 126° at 0.005 mm of Hg from 6 g of 2-benzylpyrrolidine, 4.14 g of triethylamine and 4.26 g of cyclopropanecarboxylic acid chloride.

EXAMPLE 80

2-benzyl-1-cyclopropylmethylpyrrolidine

Follow the procedure of Example 66 to obtain 3.2 g of the title compound as a colorless liquid of b.p. 100° to 105° at 0.008 mm of Hg from 5.0 g of 2-benzyl-1-cyclopropylcarbonylpyrrolidine and 0.84 g of lithium aluminum hydride.

EXAMPLE 81

1-cyclopropylmethyl-2-(4-nitrobenzyl)pyrrolidine

Follow the procedure of Example 49 to obtain the title compound as a red oil from 2-benzyl-1-cyclopropylmethylpyrrolidine.

EXAMPLE 82

2-($\alpha$-cyano-3,4-methylenedioxybenzylidene)-1-methylpyrrolidine

Add (dropwise at 80°, with stirring) a solution of 3.5 g of sodium in 80 ml of ethanol to a mixture of 16.1 g of 3,4-methylenedioxybenzylcyanide and 36 g of 2-dimethylamino-1-methyl-1-pyrrolinium-methylsulfate. Continue boiling the resulting reaction mixture for a further 2 hours. Then distil off the solvent under a vacuum and take up the residue with water/diethyl ether. Collect the ethereal layer. Dry it over sodium sulfate and concentrate it to obtain 18 g (67% of theory) of the title compound as oily liquid.

EXAMPLE 83

2-(3,4-methylenedioxybenzyl)-1-methylpyrrolidine

Follow the procedure of Example 74 to obtain the title compound as oily liquid from 2-($\alpha$-cyano-3,4-methylenedioxybenzylidene)-1-methylpyrrolidine.

EXAMPLE 84

2-(4-acetylaminobenzyl)-1-methylpyrrolidine

Add a solution of 0.78 g of acetyl chloride in 5 ml of benzene dropwise to a solution of 1.9 g of 2-(4-aminobenzyl)-1-methylpyrrolidine and 1 g of triethylamine in 10 ml of benzene. After one hour, concentrate the resulting reaction mixture. Then take it up with water and diethyl ether. Collect the organic phase and concentrate it to obtain the title compound as a yellowish oil.

EXAMPLE 85

2-dimethylamino-2-methoxy-1-methylpyrrolidine

Add (dropwise, at room temperature, with stirring) 50.0 g of 2-dimethylamino-1-methyl-1-pyrrolinium-methylsulfate to 12.65 g of sodium methylate, suspended in 120 ml of absolute diethyl ether and boil the resulting reaction mixture under reflux for 1 hour. After cooling the refluxed material, filter the precipitated salt therefrom. Draw off the ether from the filtrate and distil under a vacuum what remains of the filtrate to obtain 9.0 g of the title compound as a liquid (with a very marked tendency to decomposition) of b.p. 45° to 47° at 11 mm of Hg.

EXAMPLE 86

2-($\alpha$-cyano-4-chlorobenzylidene)-1-methylpyrrolidine

Stir 7.9 g of the title compound of Example 85 and 7.05 g of 4-chlorobenzylcyanide in 30 ml of benzene for 3 hours at 45°. Free the resulting reaction mixture from solvent by distillation to produce a dark-brown crystalline residue. Take up this residue with 10 ml of isopropanol and filter it to obtain 2.5 g of the title compound as yellowish crystals of m.p. 68° to 71°.

EXAMPLE 87

2-($\alpha$-cyano-4-nitrobenzylidene)-1-methylpyrrolidine

Stir 29.9 g of 2,2-diethoxy-1-methylpyrrolidine and 28 g of 4-nitrophenylacetonitrile in 80 ml of benzene for one hour at room temperature. Distil off the solvent from the resulting reaction mixture under a vacuum to produce a crystalline residue. Recrystallize this residue from ethanol/diethyl ether. Concentrate the mother liquor to obtain a total of 29.5 g (70% of theory) of the title compound as dark-brown shiny crystals of m.p. 67°.

EXAMPLE 88

1-methyl-2-(3-pivaloyloxybenzyl)pyrrolidine

Stir 380 mg of 2-(3-hydroxybenzyl)-1-methylpyrrolidine at 100° for 2.5 hours with 480 mg of pivaloyl chloride in 5 ml of absolute pyridine. Pour the resulting reaction mixture into 50 ml of ice water. Then add 20 ml of saturated sodium carbonate solution thereto before extracting it with diethyl ether. Dry the ether extract over sodium sulfate, distil off the solvent and distil the residue under a high vacuum to obtain 320 mg (58% of theory) of the title compound as colorless liquid of b.p. 95° to 100° at 0.002 mm of Hg.

EXAMPLE 89

2-($\alpha$-cyano-4-aminobenzylidene)-1-methylpyrrolidine

Dissolve 10 g of 2-($\alpha$-cyano-4-nitrobenzylidene)-1-methylpyrrolidine in ethanol and then reduce it with platinum/hydrogen. After completion of hydrogen uptake, filter the catalyst from the hydrogenated product, distil off the solvent and recrystallize the residue from 50 ml of ethanol to obtain 5.5 g of the title compound as light-brown crystals of m.p. 116° to 118°.

EXAMPLE 90

2-(4-aminobenzyl)-1-methylpyrrolidine

Follow the procedure of Example 46, variant a, to obtain 2.2 g of the title compound of m.p. 59° to 60° from 3.3 g of 2-($\alpha$-cyano-4-aminobenzylidene)-1-methylpyrrolidine.

EXAMPLE 91

2-(4-chlorobenzyl)-1-[3-(4-fluorobenzoyl)propyl]pyrrolidine

Boil 4 g of 2-(4-chlorobenzyl)pyrrolidine, 6.8 g of $\omega$-chloro-4-fluorobutyrophenone, 4.2 g of potassium carbonate and 20 ml of methyl ethyl ketone under reflux for 68 hours. After cooling the resulting reaction mixture to ambient temperature, add 50 ml of water and 50 ml of diethyl ether. Collect the ether phase and dry it over sodium sulfate. Concentrate the dried ether phase to a brown oil before distilling it under a high vacuum to obtain 2.0 g of the title compound as viscous light-brown oil of b.p. 188° to 192° at 0.02 mm of Hg.

EXAMPLE 92

2-(4-chlorobenzyl)-1-[4-(4-fluorophenyl)butyl]pyrrolidine

Heat 0.8 g of 2-(4-chlorobenzyl)-1-[3-(4-fluorobenzoyl)propyl]pyrrolidine to 170° for 2 hours with 1 ml of hydrazine hydrate, 0.5 g of potassium hydroxide and 5 ml of triglycol. After cooling the obtained reaction mixture to ambient temperature, add water and diethyl ether thereto. Dry the ethereal phase over sodium sulfate and distil off the solvent to obtain the title compound as brownish viscous oil.

EXAMPLE 93

2-(4-chlorobenzyl)-1-[4-(4-fluorophenyl)-4-hydroxybutyl]pyrrolidine

Stir 0.8 g of 2-(4-chlorobenzyl)-1-[3-(4-fluorobenzoyl)propyl]pyrrolidine at room temperature for 3 hours with 0.5 g of sodium borohydride in 8 ml of methanol/2 ml of water. Concentrate the resulting reaction mixture and then take up the concentrate with water/diethyl ether. Dry the ethereal phase over sodium sulfate and distil off the solvent to obtain the title compound as light-brown viscous oil.

EXAMPLE 94

2-(4-chlorobenzyl)pyrrolidine

Boil 20 g of 2-(α-cyano-4-chlorobenzylidene)pyrrolidene and 50 ml of concentrated hydrochloric acid under reflux for 2.5 hours. After cooling the obtained reaction mixture to ambient temperature, adjust its pH to from pH 5 to pH 6 with 6 N sodium hydroxide solution. Then add to the resulting mixture 50 ml of methanol and, within 20 minutes, 1.72 g of sodium borohydride. Keep the pH value constant by occasional dropwise addition of hydrochloric acid. Continue stirring for 30 minutes afterwards. Thereafter, alkalize the thus-prepared admixture with sodium hydroxide solution, extract the alkalized admixture with methylene chloride, dry the organic phase (methylene chloride extract) over sodium sulfate, concentrate the dried extract and distil the residue under a vacuum to obtain 11.12 g (63% of theory) of the title compound (b.p. 80° at 0.005 mm of Hg).

The hydrochloride (from methanol/diethyl ether) melts at 189° to 192°.

EXAMPLE 95

(−)-2-(4-chlorobenzyl)pyrrolidine

Add a solution of 37.6 g of dibenzoyl-L-tartaric acid in 250 ml of acetone to 19.57 g of 2-(4-chlorobenzyl)-pyrrolidine dissolved in 200 ml of acetone. Allow the resulting reaction mixture to stand for 12 hours and then filter off the precipitated crystals (25.8 g); $[\alpha]_{589}^{20} = -84.7°$ (25 mg/ml in methanol). Recrystallize from 75 ml methanol/100 ml acetone to obtain 15.43 g of (−)-2-(4-chlorobenzyl)pyrrolidine dibenzoyl tartrate (m.p. 178° to 179°); $[\alpha]_{589}^{20} = -88°$ (25 mg/ml in methanol). Stir 14.85 g of this salt with sodium hydroxide solution/diethyl ether until two clear phases form. Collect the ether phase and dry it over sodium sulfate. Thereafter, concentrate the dried ether phase to obtain the title compound as a colorless oil (5.0 g). Treat the colorless oil with methanol/ethereal hydrochloric acid to convert it into 4.83 g of the corresponding hydrochloride (m.p. 216° to 218°); $[\alpha]_{589}^{20} = -31.4°$ (25 mg/ml in methanol).

Isolate (from the filtrate of the crystalline dibenzoyl-tartrate) the dextro-rotatory enantiomer the hydrochloride with an optical purity of 79% $[\alpha]_{589}^{20} = +24.8°$ (25 mg/ml in methanol).

EXAMPLE 96

2-(4-chlorobenzyl)pyrrolidine

Heat 1.05 g of 5-(4-chlorobenzyl)pyrrolidin-2-one and 0.2 g of lithium aluminum hydride under reflux for 20 hours in 20 ml of tetrahydrofuran. Effect decomposition of the reaction product by admixing it with ice water. Then add 5 ml of 6 N sodium hydroxide solution to the resulting admixture and extract the thus-prepared base with diethyl ether. After drying the ether extract over sodium sulfate, concentrate it to obtain 0.7 g of the title compound as an oil. Convert the oil into the corresponding hydrochloride with methanol/ethereal hydrochloric acid; yield: 580 mg; m.p. of the hydrochloride 189° to 192°.

Condense 4-chlorobenzylcyanide with succinic acid diethyl ester in the presence of sodium ethanolate, boil the condensation product (without further purification) with a mixture of glacial acetic acid/semi-concentrated hydrochloric acid for 20 hours under reflux, convert (with hydroxylamine) the thus-obtained 5-(4-chlorophenyl)-4-oxo-pentanoic acid (m.p. 91° to 93°) into 5-(4-chlorophenyl)-4-hydroxyiminopentanoic acid (m.p. 116° to 117°), hydrogenate the latter with platinum/activated charcoal/hydrogen in acetic acid to 5-(4-chlorophenyl)-4-aminopentanoic acid and cyclize the thus-substituted pentanoic acid (through boiling in dioxane) to obtain 5-(4-chlorobenzyl)pyrrolidin-2-one (m.p. 95° to 98°).

EXAMPLE 97

2-(4-aminobenzyl)-1-methylpyrrolidine

Boil 2.04 g of 5-(4-aminobenzyl)-1-methylpyrrolidin-2-one and 0.7 g of lithium aluminum hydride under reflux for 20 hours in 20 ml of tetrahydrofuran. Decompose the resulting reaction product by admixing it with ice water. After adding 10 ml of 6 N sodium hydroxide solution to the decomposed product, extract it with diethyl ether. Dry the ether extract over sodium sulfate and concentrate it to obtain the title compound in free-base form. Convert the thus-obtained base into the dihydrochloride [m.p. (from methanol/ether) > 242° (decomp.)] with methanol/ethereal hydrochloric acid.

Methylate 5-benzylpyrrolidin-2-one with methyl iodide in the presence of potassium carbonate in ethyl methyl ketone; nitrate the thus-obtained 5-benzyl-1-methylpyrrolidin-2-one with nitric acid/sulfuric acid, pour the resulting reaction product onto ice water, extract it with methylene chloride, evaporate solvent from the extract and hydrogenate the thus-obtained 1-methyl-5-(4-nitrobenzyl)pyrrolidin-2-one with platinum/hydrogen without further purification to obtain 5-(4-aminobenzyl)-1-methylpyrrolidin-2-one.

EXAMPLE 98

2-(2,4-dinitrobenzylidene)-1-methylpyrrolidine

Stir 7.0 g of 2,4-dinitrotoluene and 9.65 g of 2,2-diethoxy-1-methylpyrrolidine for 5 hours at 40° in 50 ml of benzene. Allow the resulting reaction mixture to cool to ambient temperature. Filter off the precipitate and wash it with a little benzene and hexane to obtain 3.5 g of the title compound (m.p. 188° to 190°) in the form of black-violet crystals.

EXAMPLE 99

2-(2,4-diaminobenzyl)-1-methylpyrrolidine

Hydrogenate 3.0 g of 2-(2,4-dinitrobenzylidene)-1-methylpyrrolidine in 50 ml of ethanol with platinum/hydrogen. Filter the catalyst from the hydrogenated product and concentrate the filtrate to obtain the title compound as a yellowish viscous oil which decomposes rapidly in contact with air and under light.

EXAMPLE 100

2-(4-chlorobenzyl)-1-methylpyrrolidine

Stir 99 g of 1-methylpyrrolidinone-2 and 126 g of dimethylsulfate for 3 hours at 80°. Then cool the resulting reaction mixture to ambient temperature before dropping thereinto (within 30 minutes while cooling with ice) a solution of 150 ml of dimethylamine in 150 ml of benzene. Reflux the obtained mixture for 3 hours. Then add 121 g of benzylcyanide to it. Drop a solution of 23 g of sodium in 500 ml of ethanol into the resultant mixture over a period of 3 hours at 90° before refluxing the obtained solution for another 1½ hours. Then evaporate the main part of the solvent and dissolve the residue in 400 ml of water before extracting it with dichloromethane. Concentrate the organic phase and then heat it at reflux with 250 ml of concentrated hydrochloric acid. Make the resulting solution basic with 6 N sodium hydroxide before extracting it with dichloromethane. Concentrate the extract to a light yellow oil. Dissolve this oil in 250 ml of ethanol and then hydrogenate it over platinum on charcoal. Filter off the catalyst. Concentrate the filtrate. Distil the residue in vacuo to obtain 85 g of the title compound with a b.p. of 73° to 78° at 0.005 mm of Hg.

EXAMPLE 101

2-(4-Chlorobenzyl)-pyrrolidin

A solution of 10 mmol of n-butyllithium in n-hexane is added to a solution of 1.01 g of diisopropylamine in 100 ml of tetrahydrofuran at −78° under argon. The mixture is stirred for 5 minutes at room temperature and then cooled down again to −78°. A solution of 1.0 g of 1-nitrosopyrrolidine is added and stirring is continued for 1 hour. Then, 4.1 g of 4-chlorobenzyl bromide in a small amount of diethyl ether are added. After stirring for another 5 hours at −78° 5 ml of glacial acetic acid are added and the mixture is warmed up to room temperature, poured onto 50 ml of dichloromethane/50 ml of a saturated sodium chloride solution and well agitated. The dichloromethane phase is collected and the solvent is driven off. The remaining brown oil is solved in 50 ml of benzene, hydrogen chloride is passed into the solution for 15 minutes followed by passing through argon. The solution is rendered alkaline with aqueous sodium hydroxide and the crude pyrrolidine is extracted with diethyl ether. After removal of the solvent the remaining base is converted into the hydrochloride with methanol/ethereal hydrochloric acid.

One obtains 1.28 g (55% of theory) of m.p. 189°–192° from methanol/diethyl ether).

EXAMPLE 102

2-(4-methoxybenzyl)-pyrrolidine

A solution of 10 mmol of n-butyllithium in n-hexane is added to a solution of 1.01 g of diisopropylamine in 100 ml of tetrahydrofuran at −78° and passing argon. The mixture is stirred for 5 minutes at room temperature and then cooled again down to −78°. A solution of 1.0 g of 1-nitrosopyrrolidine is added and stirred for 1 hour. Then, 4.0 g of 4-methoxybenzyl bromide in a small amount of diethyl ether are added. After stirring for another 5 hours at −78° 5 ml of glacial acetic acid are added. The mixture is warmed up to room temperature, poured onto 50 ml of dichloromethane/50 ml of a saturated sodium chloride solution and well stirred. The dichloromethane phase is collected and the solvent is distilled off. The oily residue is solved in 50 ml of methanol. After addition of 2 g of Raney nickel freshly prepared, hydrogen is passed into the solution for 5 hours whilst stirring. The catalyst is filtered off and washed with methanol, the methanolic filtrate is concentrated. By treating the residue with ethanol/ethereal hydrochloric acid one obtains the hydrochloride of the title compound; m.p. 140°–142°.

EXAMPLE 103

2-(4-hydroxybenzyl)-1-methylpyrrolidine 3.5 g of α-(4-methoxyphenyl)-1-methylpyrrolidinyl-2-methanol, 2 g of red phosphorus and 50 ml of a 67% strength solution of hydroiodic acid are refluxed for 12 hours. Filtration and distillation of the filtrate in a vacuum removes most of the acid. The residue is taken up with diluted sodium hydroxide solution and extracted with dichloromethane. The organic phase is dried over sodium sulphate and concentrated. Recrystallisation from ethanol/charcoal yields 1.4 g of the title compound of m.p. 160°–162°.

EXAMPLE 104

Formula for 100 liters (ampoules)

| | |
|---|---|
| 1. 2-(4-chlorobenzyl)-1-methylpyrrolidine | 2.500 kg |
| 2. mannitol | 4.000 kg |
| 3. double-distilled water | ad 100 liters |

Dissolve 1 in about 80 liters of water under addition. Add 2 and adjust the solution to a pH of 7.0±0.5, and make up the volume with the remainder of the water. Sterilize the solution by filtration via a filter and fill the sterilized solution into 2 ml ampoules under sterile conditions.

EXAMPLE 105

Formula for tablets

| | |
|---|---|
| 1. 2-(4-chlorobenzyl)pyrrolidine hydrochloride | 10.0 kg |
| 2. glutamic acid | 5.0 kg |
| 3. maize starch | 38.0 kg |
| 4. lactose | 37.0 kg |
| 5. Aerosil (submicroscopic pyrogenic silica) | 1.5 kg |
| 6. sodium laurylsulfate | 2.0 kg |
| 7. gelatin | 2.5 kg |
| 8. glycerol | 0.5 kg |
| 9. talc | 2.5 kg |
| 10. magnesium stearate | 1.0 kg |

Mix 2 with 5 kg of 4 and grind the admixture to a fine particle size. Mix the ground admixture with 1, with 30 kg of 3 and with the remainder of 4, 5 and 6. Sieve the resulting combination. Then moisten the combination with a solution of 7 and 8 in 35 liters of water and force the thus-moistened material through a sieve of mesh size 1.25 mm. After drying, mix the produced granulate well with the remainder of 3, 9 and 10 before compressing the product into 200-mg (each) tablets.

EXAMPLE 106

| | |
|---|---|
| 1. 2-(4-aminobenzyl)-1-methylpyrrolidine dihydrochloride | 30.0 kg |
| 2. cellulose (Rehocel ®) | 8.5 kg |
| 3. lactose | 25.0 kg |
| 4. maize starch | 22.2 kg |
| 5. polyvinylpyrrolidone (Kollidon ® 25) | 3.0 kg |
| 6. carboxymethylcellulose (Primojel) | 8.5 kg |
| 7. talc | 2.5 kg |
| 8. magnesium stearate | 0.3 kg |

Moisten a mixture of 1, 2, 3 and 4 with 5 (dissolved in 15 liters of water), and granulate the moistened product. Thereafter, effect preliminary drying in a drying chamber at 50° before passing the material through a sieve. Dry the granulate to a relative moisture content of from 45 to 50%, after addition thereto of 6, 7 and 8 and careful mixing, compress the resultant mixture into tablets of 100 mg (each) weight.

EXAMPLE 107

Formula for tablets

| | |
|---|---|
| 1. 2-(3-hydroxybenzyl)-1-methylpyrrolidine fumarate | 25.0 kg |
| 2. cellulose (Rehocel ®) | 8.5 kg |
| 3. lactose | 30.0 kg |
| 4. maize starch | 22.2 kg |
| 5. polyvinylpyrrolidone (Kollidon ®25) | 3.0 kg |
| 6. carboxymethylcellulose (Primojel) | 8.5 kg |
| 7. talc | 2.5 kg |
| 8. magnesium stearate | 0.3 kg |

Moisten a mixture of 1, 2, 3 and 4 with 5 (dissolved in 15 liters of water), and granulate the moistened product. Thereafter, effect preliminary drying in a drying chamber at 50° before passing the material through a sieve. Dry the granulate to a relative moisture content of from 45 to 50% and, after addition thereto of 6, 7 and 8 and careful mixing, compress the resultant into tablets of 100 mg (each) weight.

The invention and its advantages are readily understood from the preceding description. It is apparent that various changes may be made in the processes and in the compounds without departing from the spirit or scope of the invention or sacrificing its material advantages. The processes, compounds and compositions hereinbefore described are merely illustrative of preferred embodiments of the invention.

What is claimed is:

1. A physiologically-active pharmacologically-acceptable compound of the formula

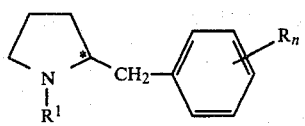

(I)

wherein
R$^1$ is a member selected from the group consisting of —H, aliphatic hydrocarbyl, alicyclic hydrocarbyl, cycloalkylalkyl aralkyl;
each R is, independently, a member selected from the group consisting of halo, alkyl, —OH, alkoxy, acyloxy, —NH$_2$, monosubstituted amino, disubstituted amino, —NO$_2$, phenyl and substituted phenyl;
n is a positive whole number of at most 4;
and any substituent bound to an aromatic carbon atom is a sterically unhindered member selected from the group consisting of halo, alkyl, —OH, alkoxy, acyloxy, —NH$_2$, substituted amino, —NO$_2$, phenyl or substituted phenyl; any substituent bound to an aliphatic carbon atom of aralkyl is a member selected from the group consisting of —OH and oxo; any substituent of substituted amino is a member selected from the group consisting of alkyl and alkanoyl having up to 5 carbon atoms;
"aliphatic" is an open-chain, linear or branched, substituted or unsubstituted, saturated or unsaturated carbon-based radical having up to 7 carbon atoms;
"hydrocarbyl" is a saturated or unsaturated organic radical having a single available bond and composed entirely of hydrogen and carbon atoms;
"aralkyl" is aryl-substituted alkyl wherein the alkyl has from 1 to 4 carbon atoms;
"aryl" is a substituted or unsubstituted monovalent unsaturated aromatic carbocyclic radical having at most 12 ring members and from 1 to 3 rings, each of which has from 5 to 7 ring members;
"acyloxy" is a radical having at most 7 carbon atoms and of one the formulae: —O—CO—R* and —O—CS—R*, wherein R* is alicyclic hydrocarbyl, cycloalkylalkyl, phenyl or aliphatic hydrocarbyl;
"alicyclic" is a saturated or aliphatically unsaturated radical having from 3 to 7 ring carbon atoms;
"alkyl" is a straight-chain or branched-chain saturated aliphatic hydrocarbon radical having from 1 to 7 carbon atoms and a single available bond; and
"cycloalkylalkyl" is alkyl (having from 1 to 4 carbon atoms) substituted by cycloalkyl (having from 3 to 7 ring carbon atoms).

2. A pharmacologically-acceptable acid-addition salt of a compound according to claim 1.

3. A compound according to claim 1 wherein R$^1$ is —H.

4. A compound according to claim 1 wherein R$^1$ is aliphatic hydrocarbyl.

5. A compound according to claim 1 wherein R$^1$ is alicyclic hydrocarbyl.

6. A compound according to claim 1 wherein R$^1$ is cycloalkylalkyl.

7. A compound according to claim 1 wherein R$^1$ is nuclearly substituted aralkyl.

8. A compound according to claim 1 wherein R$^1$ is unsubstituted aralkyl.

9. A compound according to claim 1 wherein R is halo.

10. A compound according to claim 1 wherein R is alkyl.

11. A compound according to claim 1 wherein R is —OH.

12. A compound according to claim 1 wherein R is alkoxy.

13. A compound according to claim 1 wherein R is acyloxy.

14. A compound according to claim 1 wherein R is —NH₂.

15. A compound according to claim 1 wherein R is substituted amino.

16. A compound according to claim 1 wherein R is phenyl.

17. A compound according to claim 1 wherein R is substituted phenyl.

18. A compound according to claim 1 of the formula

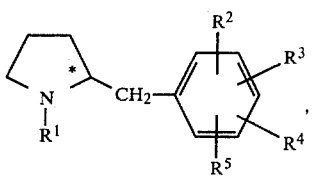

wherein
R¹ is —H, straight chain or branched aliphatic hydrocarbyl having from 1 to 5 carbon atoms, cycloalkylalkyl having from 3 to 5 ring carbon atoms and 1 or 2 carbon atoms in the alkyl chain, phenalkyl having from 1 to 4 alkyl carbon atoms or monosubstituted phenalkyl having from 1 to 4 carbon atoms in the alkyl;

R² is halo, —OH, alkyl having from 1 to 4 carbon atoms, alkoxy having from 1 to 4 carbon atoms, alkanoyloxy having from 2 to 5 carbon atoms, —NH₂, dialkylamino having 1 or 2 carbon atoms in each alkyl, nitro, phenyl or p-substituted phenyl; and each of R³, R⁴ and R⁵ is, independently, —H, halo, —OH, alkyl having from 1 to 4 carbon atoms, alkoxy having from 1 to 4 carbon atoms, alkanoyloxy having from 2 to 5 carbon atoms, —NH₂, dialkylamino having 1 or 2 carbon atoms in each alkyl or nitro;

the benzyl nucleus being unsubstituted in at least one of the 2- and 6-positions;

or a pharmacologically-acceptable acid-addition salt thereof.

19. A compound according to claim 18 wherein at least one of R³, R⁴ and R⁵ is —H.

20. A compound according to claim 19 wherein
R¹ is —H, straight-chain alkyl having from 1 to 3 carbon atoms, branched alkyl having from 3 to 5 carbon atoms, cycloalkylmethyl having from 3 to 5 ring carbon atoms, benzyl, p-halobenzyl, p-methylbenzyl or p-methoxybenzyl;
R² is halo, —OH, methoxy, —NH₂ or —NO₂;
R³ is —H, halo, —OH, methoxy, —NH₂ or —NO₂; and each of R⁴ and R⁵ is —H.

21. A compound according to claim 20 wherein R² is in the 2-, 3- or 4-position, and R³ is in one of the same positions which is not occupied by R².

22. A compound according to claim 21 wherein R¹ is —H, methyl, isopropyl, tertiary butyl, cyclopropylmethyl or benzyl.

23. A compound according to claim 22 wherein
R¹ is —H, methyl, isopropyl or cyclopropylmethyl;
R² is fluoro, chloro, hydroxy, methoxy or amino.

24. A compound according to claim 23 wherein R³ is —H.

25. A compound according to claim 24 which is a 2-(nuclearly-substituted)benzylpyrrolidine selected from the group consisting of 2-(2-chlorobenzyl)-1-methylpyrrolidine and a pharmacologically-acceptable acid-addition salt thereof.

26. A compound according to claim 24 which is a 2-(nuclearly-substituted)benzylpyrrolidine selected from the group consisting of 2-(4-chlorobenzyl)-1-methylpyrrolidine and a pharmacologically-acceptable acid-addition salt thereof.

27. A compound according to claim 24 which is a 2-(nuclearly-substituted)benzylpyrrolidine selected from the group consisting of 2-(3-methoxybenzyl)-1-methylpyrrolidine and a pharmacologically-acceptable acid-addition salt thereof.

28. A compound according to claim 24 which is a 2-(nuclearly-substituted)benzylpyrrolidine selected from the group consisting of 2-(3-hydroxybenzyl-1-methylpyrrolidine and a pharmacologically-acceptable acid-addition salt thereof.

29. A compound according to claim 24 which is a member selected from the group consisting of 2-(4-aminobenzyl)-1-methylpyrrolidine and a pharmacologically-acceptable acid-addition salt thereof.

30. A compound according to claim 24 which is a 2-(nuclearly-substituted)benzylpyrrolidine selected from the group consisting of 2-(4-chlorobenzyl)pyrrolidine and a pharmacologically-acceptable acid-addition salt thereof.

31. A compound according to claim 24 which is a 2-(nuclearly-substituted)benzylpyrrolidine selected from the group consisting of 2-(3-chlorobenzyl)-1-methylpyrrolidine and a pharmacologically-acceptable acid-addition salt thereof.

32. A compound according to claim 24 which is a 2-(nuclearly-substituted)benzylpyrrolidine selected from the group consisting of 2-(2-methoxybenzyl)-1-methylpyrrolidine and a pharmacologically-acceptable acid-addition salt thereof.

33. A CNS-stimulant or antidepressant medicament composition containing active ingredient and a physiologically-acceptable excipient or carrier therefor, the active ingredient comprising 5 to 95 percent by weight of the composition and an effective amount of a compound according to claim 1 or a pharmaceutically-acceptable acid-addition salt thereof.

34. A CNS-stimulant or antidepressant medicament composition containing active ingredient and a physiologically-acceptable excipient or carrier therefor, the active ingredient comprising from 5 to 95 percent by weight of the composition and an effective amount of a compound according to claim 23 or a pharmaceutically-acceptable acid-addition salt thereof.

35. A process which comprises administering a CNS-stimulant or antidepressant amount of a pharmacologically-acceptable compound according to claim 1 to a warm-blooded animal requiring CNS stimulation or afflicted with depression.

36. A compound according to claim 1 wherein aralkyl is phenalkyl.

* * * * *

UNITED STATES PATENT AND TRADEMARK OFFICE
CERTIFICATE OF CORRECTION

PATENT NO. : 4,279,918

DATED : July 21, 1981

INVENTOR(S) : Klaus EISTETTER, Hartmann SCHAEFER and Heinz G. MENGE

It is certified that error appears in the above–identified patent and that said Letters Patent are hereby corrected as shown below:

Column 2, line 46, "ethylenically unsat-" should read --ethylenically-unsat- --; column 3, line 7, "dichloro4" should read --dichloro-4--; column 3, line 11, "CS-R*" should read -- -CS-R*--; column 6, line 61, "radical," should read --radical;--; column 7, line 57, "The following" should start a new paragraph; column 11, line 33, "Oily suspensions" should start a new paragraph; column 11, line 43, "mon-oleate" should read --mono-oleate--; column 12, line 12, "notriptylin" should read --nortriptylin--; column 13, line 33, underneath "$R^7$" insert --(h)--; column 13, line 47, "or" should read --of--; column 14, line 49, "Synthesis" should read --*Synthesis*--; column 15, line 13, "thiolactam" should read --thiolactim--; column 16, line 10, "1976, 389; Heterocycles" should read --*1976*, 389; *Heterocycles*--; column 16, line 24, "phenyl-acetic" should read --phenylacetic--; column 16, line 66, "1974" should read --*1974*--; column 16, line 68, "K" should read --X--; column 17, line 14, "x" should read --X--; column 18, line 26, "1964" should read --*1964*--; column 18, line 49, "$R^2$, $R^2$" should read --$R^2$, $R^3$--; column 19, line 10, "tert.-butylate" should read --tert.-pentylate--; column 19, line 25, "63" should read --*63*--; column 19, line 25, "73" should read --*73*--; column 19, line 27, "1964" should read --*1964*--; column 19, line 35, "Pat. No." should read --Patent Specification--; column 19, line 55, "*Letters*" should read --*Letters,*--; column 19, line 60, "scribed *Helv.*" should read --scribed in *Helv.*--; column 20, line 3, "and end" should read --an end--; column 21, line 6, "When" should read --Where--; column 22, line 58, "-1-hexylpyrrolidine" should read -- -1-n-hexylpyrrolidine--; column 23, line 63, "$ED^{30}$" should read --$ED_{30}$--; column 23, line 66, "logesic" should read --lgesic--; column 24, line 44, "administration" should read

UNITED STATES PATENT AND TRADEMARK OFFICE
CERTIFICATE OF CORRECTION

PATENT NO. : 4,279,918

DATED : July 21, 1981

INVENTOR(S) : Klaus EISTETTER, Hartmann SCHAEFER and Heinz G. MENGE

It is certified that error appears in the above-identified patent and that said Letters Patent are hereby corrected as shown below:

--administration]--; column 24, line 62, "vis-a-vis" should read --vis-à-vis--; column 25, lines 2 through 6, "causes ptosis ("Reserpine Drive Inhibition") [Sulser, Bichel, Brodie, 1961 Med. Exp. 5, 454] in albino mice in the course of several hours; also, the normal movement activity of the animal (drive) [Domenjoz and Theobald (1959), Arch. Int. Pharmacodyn. 120/450] is considera-" should read --causes ptosis [Domenjoz and Theobald (1959), Arch. Int. Pharmacodyn. 120/450] in albino mice in the course of several hours; also, the normal movement activity of the animal (drive) ("Reserpine Drive Inhibition") [Sulser, Bickel, Brodie, 1961 Med. Exp. 5, 454] is considera- --; column 25, lines 36 through 41, "(c) Writhing test (acetic acid writhing [L. Joulou, M.-C. Bardone, R. Ducrot, B. Laffargue and G. Loiseua in "Neuro-Psycho Pharmacology", Ed. H. Brill et al., *Exerpta Medica Foundation Internat. Congress Series No.* 129, 293 to 303 (1967]: intrapertioneal injection of 0.2 ml/20 g of mouse body weight (v/v) of a 0.75%" should read --(c) Writhing test (acetic acid writhing) [Koster, Anderson, de Beer (1959) Fed. Proc. 18, 412]: intraperitoneal injection of 0.2 ml/20 g of mouse body weight of a 0.75% (v/v)--; column 25, line 56, "b." should read --B.--; column 28, line 5, "(≈100 ml)" should read --(~100 ml)--; column 28, line 6, "(≈150 ml)" should read --(~150 ml)--; column 30, line 36, "potassiumm" should read --potassium--; column 32, line 65, "dimethoxyphenyl" should read --dimethoxybenzyl--; column 34, line 42, "to" should read --at--; column 36, line 11, "60 -cyano" should read --α-cyano--; column 37,

UNITED STATES PATENT AND TRADEMARK OFFICE
CERTIFICATE OF CORRECTION

PATENT NO. : 4,279,918  
DATED : July 21, 1981  
INVENTOR(S) : Klaus EISTETTER, Hartmann SCHAEFER and Heinz G. MENGE Page 3 of 3

It is certified that error appears in the above-identified patent and that said Letters Patent are hereby corrected as shown below:

line 61, "and" should read --of--; column 38, line 16, "8 g" should read --18 g--; column 38, line 37, "alkaline 1" should read --alkaline with 1--; column 38, line 55, "amalgum" should read --amalgam--; column 39, line 2, "chloric" should read --chloride--; column 41, line 7, "o" should read --of--; column 41, line 35, "methylpyrroline" should read --methylpyrrolidine--; column 41, line 65, "$[\alpha]_{589}^{20}$" should read --$[\alpha]_{589}^{20}$--; column 42, lines 3 and 5, "$[\alpha]_{589}^{20}$" (each occurrence) should read --$[\alpha]_{589}^{20}$--; column 45, lines 58 and 61, "$[\alpha]_{589}^{20}$" (each occurrence) should read --$[\alpha]_{589}^{20}$--; column 46, line 1, "$[\alpha]_{589}^{20}$" should read --$[\alpha]_{589}^{20}$--; column 46, line 4, "enantiomer the" should read --enantiomer of 2-(4-chlorobenzyl)pyrrolidine in the form of the--; column 46, line 5, "$[\alpha]_{589}^{20}$" should read --$[\alpha]_{589}^{20}$--; column 48, line 48, "water under" should read --water and an equivalent amount of hydrochloric acid under--; column 50, line 4, "cycloalkylalkyl aralkyl" should read --cycloalkylalkyl and aralkyl--.

Signed and Sealed this

Twenty-second Day of December 1981

[SEAL]

Attest:

GERALD J. MOSSINGHOFF

Attesting Officer     Commissioner of Patents and Trademarks